US007803921B2

(12) United States Patent
Adjei et al.

(10) Patent No.: US 7,803,921 B2
(45) Date of Patent: Sep. 28, 2010

(54) SULFOTRANSFERASE 1E1 SEQUENCE VARIANTS

(75) Inventors: Araba A. Adjei, Rochester, MN (US); Eric D. Wieben, Rochester, MN (US); Richard M. Weinshilboum, Rochester, MN (US); Bianca A. Thomae, Chicago, IL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 187 days.

(21) Appl. No.: 11/861,075

(22) Filed: Sep. 25, 2007

(65) Prior Publication Data

US 2008/0182326 A1  Jul. 31, 2008

Related U.S. Application Data

(62) Division of application No. 10/354,763, filed on Jan. 30, 2003, now Pat. No. 7,288,641.

(60) Provisional application No. 60/353,066, filed on Jan. 30, 2002.

(51) Int. Cl.
*C07H 21/02* (2006.01)
*C07H 21/04* (2006.01)
*C12P 19/34* (2006.01)
*C12Q 1/68* (2006.01)

(52) U.S. Cl. .................... 536/23.1; 536/24.3; 435/91.1; 435/91.2; 435/6

(58) Field of Classification Search ....................... None
See application file for complete search history.

(56) References Cited

U.S. PATENT DOCUMENTS

| 5,451,683 | A | | 9/1995 | Barrett et al. | |
|---|---|---|---|---|---|
| 5,474,796 | A | | 12/1995 | Brennan | |
| 5,541,308 | A | * | 7/1996 | Hogan et al. | 536/23.1 |
| 5,733,729 | A | | 3/1998 | Lipshutz et al. | |
| 5,770,722 | A | | 6/1998 | Lockhart et al. | |
| 6,110,709 | A | * | 8/2000 | Ausubel et al. | 435/91.2 |
| 6,537,751 | B1 | | 3/2003 | Cohen et al. | |
| 6,812,339 | B1 | * | 11/2004 | Venter et al. | 536/24.31 |
| 2001/0036632 | A1 | * | 11/2001 | Yu et al. | 435/6 |
| 2006/0057564 | A1 | * | 3/2006 | Wang | 435/6 |

FOREIGN PATENT DOCUMENTS

| WO | WO 98/20019 | 5/1998 |
|---|---|---|
| WO | WO 99/57318 | 11/1999 |
| WO | WO 99/64630 | 12/1999 |
| WO | WO 00/20605 | 4/2000 |

OTHER PUBLICATIONS

GenBank Accession No. U08098 dated Nov. 30, 1995.
GenBank Accession No. U09552 dated May 28, 1994.
GenBank Accession No. U20514 dated Nov. 29, 1995.
GenBank Accession No. U20515 dated Nov. 29, 1995.
GenBank Accession No. U20516 dated Nov. 29, 1995.
GenBank Accession No. U20517 dated Nov. 29, 1995.
GenBank Accession No. U20518 dated Nov. 29, 1995.
GenBank Accession No. U20519 dated Nov. 29, 1995.
GenBank Accession No. U20520 dated Nov. 29, 1995.
GenBank Accession No. U20521 dated Nov. 29, 1995.
GenBank Accession No. U66036 dated May 12, 1997.
Aksoy et al., "Human Liver Estrogen Sulfotransferase: Identification by cDNA Cloning and Expression," *Biochem. Biophys. Res. Commun.*, 1994, 200(3):1621-1629.
Campbell et al., "Human Liver Phenol Sulfotransferase: Assay Conditions, Biochemical Properties and Partial Purification of Isozymes of the Thermostable Form," *Biochem. Pharmacol.*, 1987, 36(9):1435-1446.
Cibelli et al., "Cloned Transgenic Calves Produced from Nonquiescent Fetal Fibroblasts," *Science*, 1998, 280:1256-1258.
Cleland, "Computer Programmes for Processing Enzyme Kinetic Data," *Nature*, 1963, 198:463-465.
Cole et al., "The EBV-Hybridoma Technique and Its Application to Human Lung Cancer," *Monoclonal Antibodies and Cancer Therapy*, 1985, Alan R. Liss, Inc., New York, pp. 77-96.
Cote et al., "Generation of human monoclonal antibodies reactive with cellular antigens," *Proc. Natl. Acad. Sci. USA*, 1983, 80:2026-2030.
Excoffier and Slatkin, "Maximum-Likelihood Estimation of Molecular Haplotype Frequencies in a Diploid Population," *Mol. Biol. Evol.*, 1995, 12(5):921-927.
Foldes and Meek, "Rat Brain Phenolsulfotransferase—Partial Purification and Some Properties," *Biochim. Biophys. Acta*, 1973, 327:365-374.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in BRCA1 using high density oligonucleotide arrays and two-colour fluorescence analysis," *Nature Genetics*, 1996, 14:441-447.
Hempel et al., "Site-Directed Mutagenesis of the Substrate-Binding Cleft of Human Estrogen Sulfotransferase," *Biochem. Biophys. Res. Commun.*, 2000, 276:224-230.
Her et al., "Human Estrogen Sulfotransferase Gene (*STE*): Cloning, Structure, and Chromosomal Localization," *Genomics*, 1995, 29:16-23.
Hernandez et al., "Sulfation of Estrone and 17β-Estradiol in Human Liver," *Drug Metabolism and Disposition*, 1992, 20(3):413-422.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorganic & Medicinal Chemistry*, 1996, 4(1):5-23.

(Continued)

*Primary Examiner*—Sarae Bausch
*Assistant Examiner*—Katherine Salmon
(74) *Attorney, Agent, or Firm*—Fish & Richardson P.C.

(57) ABSTRACT

Isolated sulfotransferase nucleic acid molecules that include a nucleotide sequence variant and nucleotides flanking the sequence variant are described, as well as sulfotransferase allozymes. Methods for determining if a mammal is predisposed to cancer also are described.

8 Claims, 8 Drawing Sheets

OTHER PUBLICATIONS

Iida et al., "Catalog of 320 single nucleotide polymorphisms (SNPs) in 20 quinone oxidoreductase and sulfotransferase genes," *J. Hum. Genet.*, 2001, 46:225-240.

Kakuta et al., "Crystal structure of estrogen sulphotransferase," *Nature Structural Biology*, 1997, 4(11):904-908.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lewis, "PCR's Competitors are Alive and Well and Moving Rapidly Towards Commercialization," *Genetic Engineering News*, 1992, 12(9):1, 8-9.

Long et al., "An E-M Algorithm and Testing Strategy for Multiple-Locus Haplotypes," *Am. J. Hum. Genet.*, 1995, 56:799-810.

Myakishev et al., "High-Throughput SNP Genotyping by Allele-Specific PCR with Universal Energy-Transfer-Labeled Primers," *Genome Res.* 2001, 11:163-169.

Pedersen et al., "Crystal Structure of the Human Estrogen Sulfotransferase-PAPS Complex," *J. Biol. Chem.*, 2002, 277(20):17928-17932.

Prince et al., "Robust and Accurate Single Nucleotide Polymorphism Genotyping by Dynamic Allele-Specific Hybridization (DASH): Design Criteria and Assay Validation," *Genome Res.*, 2001, 11:152-162.

Schafer and Hawkins, "DNA variation and the future of human genetics," *Nature Biotechnol.*, 1998, 16:33-39.

Shastry, "Gene disruption in mice: Models of development and disease," *Mol. Cell. Biochem.*, 1998, 181:163-179.

Song et al., "Cellular Localization and Regulation of Expression of Testicular estrogen sulfotransferase," *Endocrinology*, 1997, 138:5006.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense & Nucleic Acid Drug Development*, 1997, 7:187-195.

Terwilliger and Ott, *Handbook of Human Genetic Linkage*, 1994, The Johns Hopkins University Press, Baltimore, pp. 188-193.

Underhill et al., "Detection of Numerous Y Chromosome Biallelic Polymorphisms by Denaturing High-Performance Liquid Chromatography," *Genome Res.*, 1997, 7:996-1005.

Van Loon and Weinshilboum, "Thiopurine Methyltransferase Isozymes in Human Renal Tissue," *Drug Metabolism and Disposition*, 1990, 18(5):632-638.

Van Loon et al., "Human Kidney Thiopurine Methyltransferase, Photoaffinity Labeling with S-Adenosyl-L-Methionine," *Biochem. Pharmacol.*, 1992, 44(4):775-785.

Varin et al., "Molecular characterization of two plant flavonol sulfotransferase," *Proc. Natl. Acad. Sci. USA*, 1992, 89:1286-1290.

Wakayama et al., "Full-term development of mice from enucleated oocytes injected with cumulus cell nuclei," *Nature*, 1998, 394:369-374.

Weinshilboum and Otterness, "Chapter 2-Sulfrotransferase Enzymes," *Handbook of Experimental Pharmacology*, 1994, vol. 112, Springer-Verlag Berlin Heidelberg, pp. 45-78.

Weinshilboum et al., "Sulfotransferase molecular biology: cDNAs and genes," *FASEB J.*, 1997, 11:3-14.

Weiss, "Hot Prospect for New Gene Amplifier," *Science*, 1991, 254:1292-1293.

Wilkinson, "Statistical Estimations in Enzyme Kinetics," *Biochem. J.*, 1961, 80:324-332.

Wilmut et al., "Viable offspring derived from fetal and adult mammalian cells," *Nature*, 1997, 385:810-813.

Wood et al., "Human Liver Thermolabile Phenol Sulfotransferase: cDNA Cloning, Expression and Characterization," *Biochem. Biophys. Res. Commun.*, 1994, 198:1119-1127.

Zhang et al., "Sulfuryl Transfer: The Catalytic Mechanisms of Human Estrogen Sulfotransferase," *J. Biol. Chem.*, 1998, 273(18):10888-10892.

\* cited by examiner

Figure 1 – page 1

```
aagaaaggtaatgcatttgtggattccacaaacccttggccatttattttttctaattctcttgtgt
aaattccaagtgttggtagctatcattacctgaaaaattcacagtatgctattttgtggttgggag
cagagagaagtcaggtttctaaaataataatcgaaaggtgagtgatgtttacattctttctttagc
tgtcatctgcttttttaaaattttcaggtctgcttaagagttaaaggcaaagagtttaaataggtgt
tttccaattgacatgttaagatacaacccaatgacttctttggcaggtcttaataaactgagctag
gtctgattgagggtccttgctgtcttatttctttcctcattggcttctctttcttcactccaataa
gtttattcttttgaaagttaaccatagtcatgctattatttgtcaatgagtgaataagggattctc
ccttcccagtctctcttcccaggcctcttctttctcatcttttccttttctccctccttcttcccc
aacccctgacggcagacttgggaatttgaatatgagccaaataattaaaaaaataacagcaggata
tttctacatctccatgaatgaacatgactctgtgtggttactgcagctgcaggtatgcatttacat
ctacattaactattgcatcatggacttcatgaagccaagcccccaaattaatctccacctccttct
ctggcattcaggatatataactcaccagaaacattccaaatgcAGAAGTGGTTCTCATCTTTTTTG   Exon 1
CAGCTTAAGATCTGCCTTGGTATTTGAAGAGATATAAACTAGATCAATTTCTTTCACAGGATCAAC
TAAACAGgttgtacttttttattattaatatcaatacttagattttagatatataaaatatagaat
gaaaattatgtattacaaagctcttaaaaataaaatatacaaagaccaaagtcttgattgatactt
tagttaattaatgatgtgaagcatttaaaacctttaaaataatttgttgttaaaaataatatttt
acatttatgtagtattttgttgcttattgctttaatgtaaaattacagtaccattgctatcttaaa
agtgctgaatgctggacgtgttctccattttaccaatgagaaaataaagcaagcagggtagaagga
ggtagaatagagattgacttttagttttgtgttcctgtgataagggggtcttgcaaatagggcatt
actttcatgtaagaaacttcagataaatatgacagaaatccaaagtccttggtaaataattaatat
gtaggtcattgacatatattgccttttaaatctgtgaatccttacttagtagaaactagagagctt
cttgatctaataattgaacttaacaaatatttctgaacatctactttgtgtcatagtgctggagat
tgggatagaaacatgtacaaaagtcacttttgcctcatacaggtaaatctaagaaagtagggacta
tgagaaccctatgtatctatatccaccatagtattctagcactgactacagggcctaggaaaagg
gtaggcattcacataggggagtatttgctggataaaaggcaggttggaagatgcaggaggggagtat
gcagaaagaaaggaagaaagagaggaaggagagcgggaaggaaaaacactttctgagtttaattga
atttataagtcacaatttttaacaactttttttgatgtttatttctgaacaactgacctacatactca
gaataaaaaattgacaatttctaactgaaatagatcttttgagaaaatggggatcacataggaagt
aaatccatacattgtaatatgagacaattttaccaaaaggaatagaatgagaaaagatattttatta
catgccacctactttgcctctcagaccaaaattgactatgaaggagtagctggaagtcagccaacc
acttaatgataaatctaccactcccagctgactataagccaattcttataaacttggctgaacacc
aagaaagtaattcacatgagtaagcaaaccaataggcaggacaaatcgtggtgcattttatacaca
tttcttctagtgaaagatctatttctgagactaaggagaaggcttggggaacaagtgatttattg
ataaggctaatatgcatttttggaaatagaaatctcatattttggtgacattacatctgatatgat
gtagaggaaggttttttaaaagttgagattgtcctaagggctggggcaatttatgtgtgtagaaga
acttatcaggcaggttttttgggcaaatgtgaacaggaggaagatctagaaaggctaatgtcaggaa
agacaaaatgtgttgggaagctatgtcagaaacttgaaataagctaagtttggcagttgaaaaaac
aagatactaaaggaatttgaaagctaatgaaagaaagtatgcctaattaaaaattctgttagtaac
cttgaacatgaaatagattgtcatgggatcaggagatgaattaggaaatgataaccatcttgctta
accttatcattttttagccaagtcattcaatgggagtatccactaccttattgatcgaatggggaaa
aaagtaattttaaaggtcacagaggaatcctttatactctcaagattccatttctttgatataacc
attacagtgtaattaatttcatcttttcttttaaatacattcaccaagcatttggtttatttaaaa
aaatgatacatattcaggaaatcaaaatctctgacttagatacccggcaataataatcaaatgta
atgatctttattgttatttgacatatacataattggataatttgctaaaataactgtaattctgga
cctctttgtctttttatatgccccagcaattttgaaagaaattgaagttctgtggttttatttat
cacggaataaatataattgaatatatccacatttttatttagttttaagcattttacttcataatc
acttgtgctttcctattcttttatgtgttagacatctttctaataaggttaaaaactctctatgta
ccaaaactatttgatatgcaactttactatgttttttgccccatatgtgcaacaactaagaagtgct
aggtatgtaggagggtcccgttatatacatagttgttaatggtgaaatattgttaagtacatacaa
agtataaagcagaggttttttttcagTGTACCACAATGAATTCTGAACTTGACTATTATGAAAAGT   Exon 2
TTGAAGAAGTCCATGGGATTCTAATGTATAAAGATTTTGTCAAATATTGGGATAATGTGGAAGCGT
TCCAGGCAAGACCAGATGATCTTGTCATTGCCACCTACCCTAAATCTGgtaaatctctttgttgtt
cttttttcacctaaaaataacaaacacactgtaaatggtaaatattaaggtgttcatgtcgtacac
```

Figure 1 – page 2 actcattctctatattaagaacagatgcggtagttttgatatggacatagaaaaggtagctctatt
ccatgaccacaattttttacctgtaacttgaatagtacattgagaaatggatgttgttgagcacagt
tagaaacttacataatatatactaatgaacctgtattcatcccataatgaaaatttaaaactacca
actgtttaccttatgtcattaatgttgtcgtatatacagcgtatgaccaccattttttacaggtact
ctaaaactctctttcagctcaccagccctttaagtctatctacaaaactccattttttaagcatagt
tctggagttttacaactgtagacttttagaaattagactagtccgaattcatatttcttcatctgg
ttgttccatttaccacttaaaaataaagccaaacacactaagtatgcccctagttatcttttttt
ttttttttttttttttgagacggagtctcgctctgtctcccaggctggagtgcagtggcgcgatct
ctgctcactgcaaactccgcctcctgggttcctgccattctccttcctcagcctcccgagtagctg
ggactacaggcgcccgccactgcacctggctaatttttttgatttttttagtagagacgggttttc
a  (SEQ ID NO:1)
cctttgatttacgtcttatagtctatttccaattattttccgaaccactataccattcttaagtac
caactttagattaaaaagagagactgggcttctgcctggtagaactgtttcttacctcccacaagt
ggtgaatttatgccagtaattattaaggctaagctgaaggatcacatcctctcaaaggcatttctt
gtcaaaatgtcatgtcagcagcaacaacagtagcagcagaacactgtgttatagatttcttctttg
cagttatttaaatccctgtgccatattatacaatagtatcaataaaaacaaaatttattgtagcta
ttgaacaatgtcactgacttcaaaaggcctttagctccctaaggacaggaaccagatttatcctt
gctaagttttctgacctaggacccaacatgagacataatataccatcagtaaaattttgattggaa
gcatgcttattcaagtcttcttactttttagatgtaaaaataaagtccaaaactgttagcagcttg
cacaatgtcacaattcatcatgaacaaatttggacacaggtctcaggtgtgctttactataatatt
tatctttatctcttgaggttattttgtgttctaaacataaaatatt<u>atagaaaatatttcctgag
tctgtggctattcagacacc</u>tttaaatagtattgcattggtaccttccaacttttccatccata
aatgcagcactaatgtcatcaactctacagggtcagcaggagactcaggtttatttaattttaca
g<b>GTACAACCTGGGTTAGTGAAATTGTGTATATGATCTATAAAGAGGGTGATGTGGAAAAGTGCAAA</b>  Exon 3
<b>GAAGATGTAATTTTTAATCGAATACCTTTCCTGGAATGCAGAAAAGAAAACCTCATGAATG</b>gtaac
gttcaagttgatttaaaaactatttgcatatattctaaggtgtgtatgtacatggtacaagcaat
gagattataagcaa<u>gaatggcaattagtatcaggtcttctacataagacag</u>catataaatttaaat
ttaaatttaaatcttgacaggctttgcagtatagtatgtgtacagcatatgtctggaatagagtga
ataaggacaattcttatatgccttcagcagagtttagtaatatgtaaacatttatttctctgtggg
ctaaatgtgatgatatttaaatatggagaaaaatacccataaatttttcaatgatatatgcaaaa
gtatatttaccacagattcttttaatattgtggaaaattggaaacaacctaaatgctaatcgacaa
aagaatagttaaaggttgtgtaataacactataaaatcattaacattttggatgtttcttgaaat
tgcagtttaaatataatattttgagagaaaaagatagttagaagctatcaaaacgttcatctgtgt
gcatggtattgggatggctgtaaatttgagaatataagtagatttgtatagaaggttgcttgccaa
aatatgaatgatatctctcaggtgatgaaattttatttcattttatattttctatgtaattttct
ctatctatatttctttctttcatagtaagtattattatgaacacaatatagaatcttttaattttt
aattttgtgaatatatattagatgtaaatattaatggggcacatgagatgttttgatat<u>aggcat
gcaatgcataataattacaccatggaaatggggt</u>gtccattccctcaagaa<u>t</u>ttatactttgtgt
tacacacaatctaattacaatatagaatcttagaattacttct<u>a</u>ttttacaaatatctatataaat
ccacataaaatagttacaattttttgaagttgcttaacccttcacttttttaaaaatcag<b>GAGTAAAAC</b>  Exon 4
<b>AATTAGATGAGATGAATTCTCCTAGAATTGTGAAGACTCATTTGCCACCTGAACTTCTTCCTGCCT</b>
<b>CATTTTGGGAAAAGGATTGTAAG</b>gtaaccagagtcaagtgttctcaaaacttcatccaattccaag
aaatgatagagtgatctcatcagtt<u>a</u>tacacacttgtttatttattctttcattgaatctatagac
acttaacaaatgtggaataaatacagtca<u>a</u>tattg<u>tcagagagtctatattttaattccaactctg
tcttttgccag</u>atgtggttctaaaaagtccagttagactccctaagcctaagttttacatctgta
gaagaaagataataataacatcttttttcatggaattgttataaggattacatgataatgcttataa
agtgcttcacctaattcctagcatattgtaaacaacaaatgttagctacttttgtatttgttgtta
ttactaattgtattgaatatcctcccttttgcaaaatactgtgcttggtgctgttaggcatgcaaat
gaaccataaaaggataggtcagataactgtcatataataactatgtattgagtgcctattatgtgt
tagggacataagagtaagacacatgcaagccttgtcttcatggacacctagtccatttcagaaaaa
ggacaggttaacagacaagacaaaaagtatcataggtcaagtaagagagagaattcaaactcagac
actgggggtagggaaggcatccaggagcaacatctcagctgatattt  (SEQ ID NO:2)
tcttactgccaaaactagaaactaaaaccacagttttctgaaaactaattcattggtatttcttct

Figure 1 – page 3

```
gcatgtaaaatggaaactaacaaggtgttggcagaggttatattttcacctcataaaatgtttttt
tcctgtaatattgaaagtgaagagacctcagaactattttttttaattatgtggagtgatggtgt
agtataaagaccagagcactgtatagttgactgaatgatatgccaaatggtttactctcattgatt
tactctcaatgctatattatcactaaatttcagcttaatctcttcacttatacattgagaataata
aataatgtaactgacttaatttatattgataaaatttacaacactcaaatgaggtattatgtgtga
aaatggcataataatgttgttctgtttgtagtgagaacaaagagaacaacactacaaaaaccactg
tcacctcaggttattgaagatgtctttataaataattgtacatgtcttatgcatttgtaaaatta
atgtgtattatgtttatatttgaaaatgtaaatccttttaaaaaaatcttgatgagactgtttga
aaaaaatgttaagtggtttaatatacaatttcatcctcttagATAATCTATCTTTGCCGGAATGCA  Exon 5
AAGGATGTGGCTGTTTCCTTTTATTATTTCTTTCTAATGGTGGCTGGTCATCCAAATCCTGGATCC
TTTCCAGAGTTTGTGGAGAAATTCATGCAAGGACAGGgtaggaacagcttctttacactgaattt
ttttcaaggttttataagacaaatgccatctccaagtaaaagttttaactgttctggtacgtttt
cttccctgattcatagttaaaacacagaaatctaaaggcgcctggaggtttagagcaagcatactg
tgtccagatgtagaaggcaaattgcagaatctgagcactctggtccaacacctaaaaataaatata
tagaattatgtttgggagctgggggtagcaatttttattctccaagattgagactcagtgtctgatt
ttctgccttgtctcttttagtagaaacaaatgttttacaccgtattattacaactctattgaaca
atgggttggggagagattagagaagagagaatgttcacttatttccaataaaattgccaggttcta
tatgaatatggaatttaacaagaagtttgactatctacaaaactcttcctcattctaccccgagtg
caatctgaatattttaaaccaggtttctcaaatttgttaagggttacccgaagcagatattctgga
aaattttcgttttatttaacactttactaaagtgttagatttgagaagaaagggtgcagnata
gtctagtatctaaagaaggccattctgatcatgtagtaacaattataaagaaaataataatgtgtt
ttcatatccacagatgataatattgactcaagacaaataaggtatatgtgctttgtgtttgttgct
acattttgggaaaattttgctaaagcataatgagtaatacatatgtcttaagattgtcaagacct
ccactgcagggcagagaaatataattttgcatcactgcaaagggagaaataagatcactataaatt
tcactgtagaacatttctgtaaggaaaaattccctaatggagtcaaagaacagaggaggcataca
atgacttcaggcaaagcagaaccttttgactcacacaacattatattattttgtcagctttatatt
ttatgaaacatttttactatgagtgaggcaagagaaagaaaaaggaagagacagcatttggttata
ttacatcatttctaaaatctaatttcctggagtgagaatgacactaagggtacctacgagaacatt
ccttcccatgtaaactaatagtgtaataaatactcatatagttactagttttagttgccaaaccta
gtttgtaaatggtaaatttgagaccagaactatattcttatgactatcagaccactgatagtttca
ctaagtcaactcccttcactaacaatttgattctacacacacacacacacacacacaccagttt
caacaattttctcataagctttaaatcaaattgatgagagaactttccctgttttctgtcataaa
ctacattatctgataaagttcatactattttacatacatagattatttaacatactttgcctctc
ttgctgcagagaactttgcttaagatatacagctgatctattctaatttcatgattatctatttat
atttatttgttgttattgttgcttgaacactagttttcgagcagttttagagatgataccacttt
acactgtttttctctgtaattttagTTCCTTATGGTTCCTGGTATAAACATGTAAAATCTTGGTGG  Exon 6
GAAAAGGGAAAGAGTCCACGTGTACTATTTCTTTTCTACGAAGACCTGAAAGAGgtgaggaactgg
gaacacataagcaacttggtaatttctaagatgttagcatttgaaaatactctggatacaaaata
ttcctttaaataaatgatgacagccatctcgtaaattttttaaaggaaaggaccaaaataatacag
atactttagcatagatttgaagctagcaaataaaaatattctgaaaataaatacatttaaaccac
aagtctcaaaaatttcaaagaaaaaatttgaaagaacttgacttcatgaatcaataacacacacac
ataggcacacacacacacacattcacacacaaggaatcaacatgggcaagcaattaactggtctgc
aaatgtagagatgttgcaattgttagataggtcctataaaataaccatgcttaatatgtttaaata
aataaagatgaaattttaaaaattacaaagaaacaaaaactattaaaattgacagagcagatttg
aaaaaaaatagccaaatacaatttctaaaaataactaaaaaaatatgaaaaattaagagatgggtt
caataatagattagacatggctacatagtgaattattgaagtaaaagatggagctaaggaaattct
atagaatgtagcacagtgagataaataggctatttgatgaaagtaatggttcttactaagtatta
gcatttaaaaaataa   (SEQ ID NO:3)
agcaaaacagggtcatctacccaaaattagaatagccaaggatattatcctaaataagttgataaa
taagctgaaatcgaaaaggcaaactacaatttattgagcagagaatttagaaacagcatttgattg
gcatagagagaaatgtgcacttgaatacacattgcggttagtattgcaaatagttgcactgagaga
tatagctgaataatggtgtatattataggagtggcacagatatggggatgtttgtagctatggtgt
acagacaactgatgttgcattgtgagtatttgactttttacacctttcttaatctttcttgtttc
```

Figure 1 – page 4

```
tttgtttctcactaattacaccaataaattaggagaaaaatgaaaattgcctgtatatctttatcc
cccaaacttgatttttcacaggggactttaggttttgagtatgatgtttgttttcatagacaacat
ctattaagtgtgattatgcatcaaggactacaataagcattcacaaacatctcatttagtttttg
aataatcttaaagtatcttttataagcattttatggatgaggaaaattatacttaaaacagcttt
ataaaattcccccaattagatttctcattagaaatctaattctaatatcagtaggagaaaagagaa
aggtttatttttctctttcatttagatagtgatttattcagttttagcaatttagttctcaaaac
attttctctccctagGATATCAGAAAAGAGGTGATAAAATTGATACATTTCCTGGAAAGGAAGCCA   Exon 7
TCAGAGGAGCTTGTGGACAGGATTATACATCATACTTCGTTCCAAGAGATGAAGAACAATCCATCC
ACAAATTACACAACACTGCCAGACGAAATTATGAACCAGAAATTGTCGCCCTTCATGAGAAAGGgt
gagaaaaatgtggtttgcctcgatactagaggaagtcacaaggtgacatggttataggcaaaaatc
tagtgaggtattttaatgcctatgaacccagcttaagttttcttcagcagtctttcatatttgaat
acactctttaagttacacttctattacattgcaattacctgttgattatttattatatgcatcata
ttatgttaaaataactagcagactcctcaatctcagcattggaaatagtatcacactctactagct
gtaatttaccaagcctatgtgcctcagtgttacaacatgtatcatatagttcctttaagttctaac
cagaaattccgcagaaagatttattcctctctcttttgagttgaagaaataagtttagaatagt
ttgtcaacatttttaacaagtggcaaacacctttcaagggtaagtggcaaaaaatagaaattcaa
atatagctctgtttagcaaaaaatatcaacatataaggagaaaaaaattctatttgaagggaaaca
tagcctgatgagatatagccagttaacaaatttaaaggcatgtaagatattcagatattcagagca
ctgggacaccagtctatttatatgaggaagcagaaacaaacagaatagaatcaaatcttgctct
ttgaaccatactgtcagtgagagtcagggaatttgtaaaataacaaacctgccactg   (SEQ ID NO:4)
aaaaaaaaaaagatgaattccttctgcaaggtgagtgttggaagtatgttaaaaagcaaacagg
aaaagcctgctggactattataattacccagatgagaaacactctctggctggcagtagcagaagt
gtttaagaggcagtagatataaagaaagcctgaatataatgaattagatgttgtggttaagagaat
aacgtccaagcttatgtgtagatacctggtgttgactctacacaggtcattaaaatgtaaatggag
aaaacacaatatgctaaggaataaaatgaatttattttgaactaattgtatttggaaaatttgga
cattttcaggtggcaaaatcatgtaggcagttgtatataaagcataagtctggatttagtgcta
tcagcattaagatgatatttaacaccttgagagtgggtaaaacatggatcttatcctgggagcccc
aacagctgagatgaaacttcagaagaaaaataaagtaaatggcataagaagaaagaatcagagaat
taaatttgttgtttttttaaaccaattaggacaaatccatctttgtaagcccaaaaaagtatatca
ttaaaggtatacatttgattcctaaaattgagaattacaagtataatatttgattaggtgttaatg
aaagtgatgaaattagcaaacctaatgattcttttggaagacttaatatttattgagctttcttt
tttgttacagGAATTACAGGAGACTGGAAAAATCACTTTACAGTAGCCCTGAATGAAAAATTTGAT   Exon 8
AAACATTATGAGCAGCAAATGAAGGAATCTACACTGAAGTTTCGAACTGAGATCTAAGAAGGTCTT
TCTTTACTTAACATATCTGATATTAAAGATTTCTTTTCATTATTCtccacttttttcttattttaga
ttgctagaaaagacataatcatggattatgttgacattttcttttttaaattttttgtttaacttttt
ttttttttttttgagacagagtctcactctgttgcctaggctggaggacagtggcacaatcatggc
tgattgcagccttgacctccttgactcaattgatcctcccatctcagcctcccaagtagctaggac
tacagacatgtgcaaccatgtttggctaatttttttaatgtttttttgtagagatgaggtcttatt
atattgtccaggctggtcttgaattcctgggctcaagcttcccaagtagctgcaacaacaggcaca
caccaccatgctcaactaatttatttctattttttgtatagacaggggcttgctatagtgtccag
gctggtctgaaacccttgagctcaagtgatcttcccacaccagcctcccaaaatactgggattaca
ggcttgagcctccatgcctggccccaggtaacatgtttattgagctgtacatgcatatgagaaata
agaaacttttttttcctactatcatctcttaaatttggtttctttttttcttttgcttcctcttct
tcttttctattttttataaatatcatgcacaactataacctatgggaatgatgtagtaacccagat
tattcatcttgttagagttgtattaaaaataaacaagcatttcaaattattttttgtgattgatttt
ccatttagtaggacattagtatataataaaaatggtgcatgaactttgaagactctggaagaaaga
atgaaataatatataaatagggggcataactata   (SEQ ID NO:5)
```

Figure 2A

```
   1 agaagtggtt ctcatctttt tttgcagctt aagatctgcc ttggtatttg aagagatata
  61 aactagatca atttctttca caggatcaac taaacagtgt accacaatga attctgaact
 121 tgactattat gaaaagtttg aagaagtcca tgggattcta atgtataaag attttgtcaa
 181 atattgggat aatgtggaag cgttccaggc aagaccagat gatcttgtca ttgccaccta
 241 ccctaaatct ggtacaacct gggttagtga aattgtgtat atgatctata agagggtga
 301 tgtggaaaag tgcaaagaag atgtaatttt taatcgaata cctttcctgg aatgcagaaa
 361 agaaaacctc atgaatggag taaaacaatt agatgagatg aattctccta gaattgtgaa
 421 gactcatttg ccacctgaac ttcttcctgc ctcatttgg gaaaaggatt gtaagataat
 481 ctatctttgc cggaatgcaa aggatgtggc tgtttccttt tattatttct ttctaatggt
 541 ggctggtcat ccaaatcctg gatcctttcc agagtttgtg gagaaattca tgcaaggaca
 601 ggttccttat ggttcctggt ataaacatgt aaaatcttgg tgggaaaagg gaaagagtcc
 661 acgtgtacta tttctttct acgaagacct gaaagaggat atcagaaaag aggtgataaa
 721 attgatacat ttcctggaaa ggaagccatc agaggagctt gtggacagga ttatacatca
 781 tacttcgttc aagagatga agaacaatcc atccacaaat tacacaacac tgccagacga
 841 aattatgaac cagaaattgt cgcccttcat gagaaaggga attacaggag actggaaaaa
 901 tcactttaca gtagccctga atgaaaaatt tgataaacat tatgagcagc aaatgaagga
 961 atctacactg aagtttcgaa ctgagatcta agaaggtctt tctttactta acatatctga
1021 tattaaagat ttctttcat tattca
```

(SEQ ID NO:6)

Figure 2B

```
  1 MNSELDYYEK FEEVHGILMY KDFVKYWDNV EAFQARPDDL VIATYPKSGT TWVSEIVYMI
 61 YKEGDVEKCK EDVIFNRIPF LECRKENLMN GVKQLDEMNS PRIVKTHLPP ELLPASFWEK
121 DCKIIYLCRN AKDVAVSFYY FFLMVAGHPN PGSFPEFVEK FMQGQVPYGS WYKHVKSWWE
181 KGKSPRVLFL FYEDLKEDIR KEVIKLIHFL ERKPSEELVD RIIHHTSFQE MKNNPSTNYT
241 TLPDEIMNQK LSPFMRKGIT GDWKNHFTVA LNEKFDKHYE QQMKESTLKF RTEI
```

(SEQ ID NO:7)

60122032.doc

SEQUENCE LISTING

<160> NUMBER OF SEQ ID NOS: 31

<210> SEQ ID NO 1
<211> LENGTH: 4159
<212> TYPE: DNA
<213> ORGANISM: Homo sapiens

<400> SEQUENCE: 1

```
aagaaaggta atgcatttgt ggattccaca aacccttggc catttatttt tctaattctc      60
ttgtgtaaat tccaagtgtt ggtagctatc attacctgaa aaattcacag tatgctattt     120
tgtggttggg agcagagaga agtcaggttt ctaaaataat aatcgaaagg tgagtgatgt     180
ttacattctt tctttagctg tcatctgctt tttaaaattt tcaggtctgc ttaagagtta     240
aaggcaaaga gtttaaatag gtgttttcca attgacatgt taagatacaa cccaatgact     300
tctttggcag gtcttaataa actgagctag gtctgattga gggtccttgc tgtcttattt     360
ctttcctcat tggcttctct ttcttcactc caataagttt attcttttga aagttaacca     420
tagtcatgct attatttgtc aatgagtgaa taagggattc tcccttccca gtctctcttc     480
ccaggcctct tctttctcat cttttccttt tctccctcct tcttccccaa cccctgacgg     540
cagacttggg aatttgaata tgagccaaat aattaaaaaa ataacagcag gatatttcta     600
catctccatg aatgaacatg actctgtgtg gttactgcag ctgcaggtat gcatttacat     660
ctacattaac tattgcatca tggacttcat gaagccaagc ccccaaatta atctccacct     720
ccttctctgg cattcaggat ataaactcac cagaaacatt ccaaatgcag aagtggttct     780
catctttttt tgcagcttaa gatctgcctt ggtatttgaa gagatataaa ctagatcaat     840
ttctttcaca ggatcaacta aacaggttgt actttttttat tattaatatc aatacttaga     900
ttttagatat ataaaatata gaatgaaaat tatgtattac aaagctctta aaaataaaat     960
atacaaagac caaagtcttg attgatactt tagttaatta atgatgtgaa gcatttaaaa    1020 cctttaaaa taatttgttg ttaaaaataa tattttacat ttatgtagta ttttgttgct    1080
tattgcttta atgtaaaatt acagtaccat tgctatctta aaagtgctga atgctggacg    1140
tgttctccat tttaccaatg agaaaataaa gcaagcaggg tagaaggagg tagaatagag    1200
attgactttt agttttgtgt tcctgtgata aggggtcttg caaataggg cattactttc      1260 atgtaagaaa cttcagataa atatgacaga aatccaaagt ccttggtaaa taattaatat    1320
gtaggtcatt gacatatatt gccttttaaa tctgtgaatc cttacttagt agaaactaga    1380
gagcttcttg atctaataat tgaacttaac aaatatttct gaacatctac tttgtgtcat    1440
agtgctggag attgggatag aaacatgtac aaaagtcact tttgcctcat acaggtaaat    1500
ctaagaaagt agggactatg agaaccccta tgtatctata tccaccatag tattctagca    1560
```

-continued

```
ctgactacag ggcctaggaa aagggtaggc attcacatag ggagtatttg ctggataaaa    1620
ggcaggttgg aagatgcagg aggggagtat gcagaaagaa aggaagaaag agaggaagga    1680
gagcgggaag gaaaaacact ttctgagttt aattgaattt ataagtcaca attttaacaa    1740
cttttttgat gtttatttct gaacaactga cctacatact cagaataaaa aattgacaat    1800
ttctaactga aatagatctt ttgagaaaat ggggatcaca taggaagtaa atccatacat    1860
tgtaatatga gacaatttac caaaaggaat agaatgagaa aagatatttt attacatgcc    1920
acctactttg cctctcagac caaaattgac tatgaaggag tagctggaag tcagccaacc    1980
acttaatgat aaatctacca ctcccagctg actataagcc aattcttata aacttggctg    2040
aacaccaaga aagtaattca catgagtaag caaaccaata ggcaggacaa atcgtggtgc    2100
attttataca catttcttct agtgaaagat ctattttctg agactaagga aaggcttgg     2160
ggaacaagtg atttattgat aaggctaata tgcattttgg aaatagaaat ctcatatttt    2220
tggtgacatt acatctgata tgatgtagag gaaggttttt taaaagttga gattgtccta    2280
agggctgggg caatttatgt gtgtagaaga acttatcagg caggttttg ggcaaatgtg     2340
aacaggagga agatctagaa aggctaatgt caggaaagac aaaatgtgtt gggaagctat    2400
gtcagaaact tgaaataagc taagtttggc agttgaaaaa acaagatact aaaggaattt    2460
gaaagctaat gaaagaaagt atgcctaatt aaaaaattctg ttagtaaccct tgaacatgaa   2520
atagattgtc atgggatcag gagatgaatt aggaaatgat aaccatcttg cttaaccta     2580
tcattttttag ccaagtcatt caatgggagt atccactacc ttattgatcg aatggggaaa   2640
aaagtaattt taaaggtcac agaggaatcc tttatactct caagattcca tttctttgat    2700
ataaccatta cagtgtaatt aatttcatct tttcttttaa atacattcac caagcatttg    2760
gtttatttaa aaaatgata catattcagg aaatcaaaaa tctctgactt agatacccgg     2820
caataataat caaatgtaat gatctttatt gttatttgac atatacataa ttggataatt    2880
tgctaaaata actgtaattc tggacctctt tgtcttttta tatgccccag caattttgaa    2940
agaaattgaa gttctgtggt ttttatttat cacggaataa atataattga atatatccac    3000
attttatttt agttttaagc attttacttc ataatcactt gtgctttcct attcttttat    3060
gtgttagaca tctttctaat aaggttaaaa actctctatg taccaaaact atttgatatg    3120
caactttact atgttttgc cccatatgtg caacaactaa gaagtgctag gtatgtagga     3180
gggtcccgtt atatacatag ttgttaatgg tgaaatattg ttaagtacat acaaagtata    3240
aagcagaggt tttttttcag tgtaccacaa tgaattctga acttgactat tatgaaaagt    3300
ttgaagaagt ccatgggatt ctaatgtata aagattttgt caaatattgg gataatgtgg    3360
aagcgttcca ggcaagacca gatgatcttg tcattgccac ctaccctaaa tctggtaaat    3420
ctctttgttg ttctttttc acctaaaaat aacaaacaca ctgtaaatgg taaatattaa     3480
ggtgttcatg tcgtacacac tcattctcta tattaagaac agatgcggta gttttgatat    3540
ggacatagaa aaggtagctc tattccatga ccacaatttt tacctgtaac ttgaatagta    3600
cattgagaaa tggatgttgt tgagcacagt tagaaactta cataatatat actaatgaac    3660
ctgtattcat cccataatga aaatttaaaa ctaccaactg tttaccttat gtcattaatg    3720
ttgtcgtata tacagcgtat gaccaccatt tttacaggta ctctaaaact ctctttcagc    3780
tcaccagccc tttaagtcta tctacaaaac tccattttta agcatagttc tggagtttta    3840
caactgtaga cttttagaaa ttagactagt ccgaattcat atttcttcat ctggttgttc    3900
```

-continued

| | |
|---|---|
| catttaccac ttaaaaataa agccaaacac actaagtatg cccctagtta tctttttttt | 3960 |
| tttttttttt tttttttgaga cggagtctcg ctctgtctcc caggctggag tgcagtggcg | 4020 |
| cgatctctgc tcactgcaaa ctccgcctcc tgggttcctg ccattctcct tcctcagcct | 4080 |
| cccgagtagc tgggactaca ggcgcccgcc actgcacctg gctaattttt ttgaattttt | 4140 |
| tagtagagac gggttttca | 4159 |

<210> SEQ ID NO 2
<211> LENGTH: 2687
<212> TYPE: DNA
<213> ORGANISM: Homo sapiens

<400> SEQUENCE: 2

| | |
|---|---|
| cctttgattt acgtcttata gtctatttcc aattattttc cgaaccacta taccattctt | 60 |
| aagtaccaac tttagattaa aaagagagac tgggcttctg cctggtagaa ctgtttctta | 120 |
| cctcccacaa gtggtgaatt tatgccagta attattaagg ctaagctgaa ggatcacatc | 180 |
| ctctcaaagg catttcttgt caaaatgtca tgtcagcagc aacaacagta gcagcagaac | 240 |
| actgtgttat agatttcttc tttgcagtta ttttaaatccc tgtgccatat tatacaaatag | 300 |
| tatcaataaa aacaaaattt attgtagcta ttgaacaatg tcactgactt caaaaggcct | 360 |
| ttagctccct aaggacagga accagattta tcctttgcta agttttctga cctaggaccc | 420 |
| aacatgagac ataatatacc atcagtaaaa ttttgattgg aagcatgctt attcaagtct | 480 |
| tcttactttt tagatgtaaa aataaagtcc aaaactgtta gcagcttgca caatgtcaca | 540 |
| attcatcatg aacaaatttg gacacaggtc tcaggtgtgc tttactataa tatttatctt | 600 |
| tatctcttga ggttattttt gtgttctaaa cataaaatat tatagaaaat atttcctgag | 660 |
| tctgtggcta ttcagacacc ctttaaatag tattgcattg gtaccttcca acttttttcca | 720 |
| tccataaatg cagcactaat gtcatcaact ctacagggtc agcaggagac tcaggttttat | 780 |
| ttaatttta caggtacaac ctgggttagt gaaattgtgt atatgatcta taagagggt | 840 |
| gatgtggaaa agtgcaaaga agatgtaatt tttaatcgaa tacctttcct ggaatgcaga | 900 |
| aaagaaaacc tcatgaatgg taacgttcaa gttgatttta aaaactattt gcatatattc | 960 |
| taaggtgtgt atgtacatgg tacaagcaat gagattataa gcaagaatgg caattagtat | 1020 |
| caggtcttct acataagaca gcatataaat ttaaatttaa atttaaatct tgacaggctt | 1080 |
| tgcagtatag tatgtgtaca gcatatgtct ggaatagagt gaataaggac aattcttata | 1140 |
| tgccttcagc agagtttagt aatatgtaaa catttatttc tctgtgggct aaatgtgatg | 1200 |
| atattttaaa tatggagaaa ataccccata aattttccaa tgatatatgc aaaagtatat | 1260 |
| ttaccacaga ttctttttaat attgtggaaa attggaaaca acctaaatgc taatcgacaa | 1320 |
| aagaatagtt aaaggttgtg taataacact ataaaatcat taacatttt ggatgtttct | 1380 |
| tgaaattgca gtttaaatat aatatttga gagaaaaga tagttagaag ctatcaaaac | 1440 |
| gttcatctgt gtgcatggta ttgggatggc tgtaaatttg agaatataag tagatttgta | 1500 |
| tagaaggttg cttgccaaaa tatgaatgat atctctcagg tgatgaaatt ttatttcatt | 1560 |
| ttatattttt ctatgtaatt ttctctatct atatttcttt ctttcatagt aagtattatt | 1620 |
| atgaacacaa tatagaatct tttaattttt aattttgtg aatatatatt agatgtaaat | 1680 |
| attaatgggg cacatgagat gttttgatat aggcatgcaa tgcataataa ttacaccatg | 1740 |
| gaaaatgggg tgtccattcc ctcaagaatt tatactttgt gttacacaca atctaattac | 1800 |
| aatatagaat cttagaatta cttctatttt acaaatatct atataaatcc acataaatag | 1860 |

-continued

```
ttacaattt  tgaagttgct  taacctttac  ttttttaaaa  atcaggagta  aaacaattag    1920
atgagatgaa  ttctcctaga  attgtgaaga  ctcatttgcc  acctgaactt  cttcctgcct    1980
cattttggga  aaaggattgt  aaggtaacca  gagtcaagtg  ttctcaaaac  ttcatccaat    2040
tccaagaaat  gatagagtga  tctcatcagt  tatacacact  tgtttattta  ttctttcatt    2100
gaatctatag  acacttaaca  aatgtggaat  aaatacagtc  aatattgtca  gagagtctat    2160
attttaattc  caactctgtc  ttttgccaga  tgtggttcta  aaaagtccag  ttagactccc    2220
taagcctaag  ttttacatc   tgtagaagaa  agataataat  aacatctttt  tcatggaatt    2280
gttataagga  ttacatgata  atgcttataa  agtgcttcac  ctaattccta  gcatattgta    2340
aacaacaaat  gttagctact  tttgtatttg  ttgttattac  taattgtatt  gaatatcctc    2400
cctttgcaaa  atactgtgct  tggtgctgtt  aggcatgcaa  atgaaccata  aaaggatagg    2460
tcagataact  gtcatataat  aactatgtat  tgagtgccta  ttatgtgtta  gggacataag    2520
agtaagacac  atgcaagcct  tgtcttcatg  gacacctagt  ccatttcaga  aaaaggacag    2580
gttaacagac  aagacaaaaa  gtatcatagg  tcaagtaaga  gagagaattc  aaactcagac    2640
actgggggta  gggaaggcat  ccaggagcaa  catctcagct  gatattt                   2687
```

<210> SEQ ID NO 3
<211> LENGTH: 3183
<212> TYPE: DNA
<213> ORGANISM: Homo sapiens
<220> FEATURE:
<221> NAME/KEY: misc_feature
<222> LOCATION: 1383
<223> OTHER INFORMATION: n = A,T,C or G

<400> SEQUENCE: 3

```
tcttactgcc  aaaactagaa  actaaaacca  cagttttctg  aaaactaatt  cattggtatt      60
tcttctgcat  gtaaaatgga  aactaacaag  gtgttggcag  aggttatatt  ttcacctcat     120
aaaatgtttt  tttcctgtaa  tattgaaagt  gaagagacct  cagaactatt  ttttttttaat    180
tatgtggagt  gatggtgtag  tataaagacc  agagcactgt  atagttgact  gaatgatatg    240
ccaaatggtt  tactctcatt  gatttactct  caatgctata  ttatcactaa  atttcagctt     300
aatctcttca  cttatacatt  gagaataata  aataatgtaa  ctgacttaat  ttatattgat    360
aaaatttaca  acactcaaat  gaggtattat  gtgtgaaaat  ggcataataa  tgttgttctg     420
tttgtagtga  gaacaaagag  aacaacacta  caaaaccac   tgtcacctca  ggttattgaa     480
gatgtcttta  taaataattg  tacatgtctt  atgcattttg  taaaattaat  gtgtattatg     540
tttatatttg  aaaatgtaaa  tccttttaa   aaaaatcttg  atgagactgt  ttgaaaaaa     600
tgttaagtgg  tttaatatac  aatttcatcc  tcttagataa  tctatctttg  ccggaatgca     660
aaggatgtgg  ctgtttcctt  ttattattc   tttctaatgg  tggctggtca  tccaaatcct     720
ggatcctttc  cagagtttgt  ggagaaattc  atgcaaggac  agggtaggaa  cagcttcttt     780
acactgaatt  tttttcaag   gttttataag  acaaatgcca  tctccaagta  aaagtttta     840
actgttctgg  tacgttttct  tccctgattc  atagttaaaa  cacagaaatc  taaaggcgcc     900
tggaggttta  gagcaagcat  actgtgtcca  gatgtagaag  gcaaattgca  gaatctgagc     960
actctggtcc  aacacctaaa  aataaatata  tagaattatg  tttgggagct  ggggggtagca   1020
attttattct  ccaagattga  gactcagtgt  ctgattttct  gccttgtctc  ttttttagtag   1080
aaacaaatgt  tttacaccgt  attattacaa  ctctattgaa  caatgggttg  gggagagatt   1140
```

-continued

```
agagaagaga gaatgttcac ttatttccaa taaaattgcc aggttctata tgaatatgga    1200
atttaacaag aagtttgact atctacaaaa ctcttcctca ttctaccccg agtgcaatct    1260
gaatatttta aaccaggttt ctcaaatttg ttaagggtta cccgaagcag atattctgga    1320
aaatttttcg ttttattta acacttttac taaagtgtta gatttgagaa gaaagggtgc    1380
agnatagtct agtatctaaa gaaggccatt ctgatcatgt agtaacaatt ataaagaaaa    1440
taataatgtg ttttcatatc cacagatgat aatattgact caagacaaat aaggtatatg    1500
tgctttgtgt ttgttgctac attttgggaa aattttttgct aaagcataat gagtaataca    1560
tatgtcttaa gattgtcaag acctccactg cagggcagag aaatataatt ttgcatcact    1620
gcaaagggag aaataagatc actataaatt tcactgtaga acattttctg taaggaaaaa    1680
ttccctaatg gagtcaaaga acagaggagg catacaatga cttcaggcaa agcagaacct    1740
tttgactcac acaacattat attattttgt cagctttata ttttatgaaa cattttact    1800 atgagtgagg caagagaaag aaaaaggaag agacagcatt tggttatatt acatcatttc    1860
taaaatctaa tttcctggag tgagaatgac actaagggta cctacgagaa cattccttcc    1920
catgtaaact aatagtgtaa taaatactca tatagttact agttttagtt gccaaaccta    1980
gtttgtaaat ggtaaatttg agaccagaac tatattctta tgactatcag accactgata    2040
gtttcactaa gtcaactccc ttcactaaca atttgattct acacacacac acacacacac    2100
acacaccagt ttcaacaatt ttctcataag ctttaaatca aattgatgag gaactttcc    2160 ctgtttttct gtcataaact acattatctg ataaagttca tactattttt acatacatag    2220
attatttaac atactttgcc tctcttgctg cagagaactt tgcttaagat atacagctga    2280
tctattctaa tttcatgatt atctatttat atttatttgt tgttattgtt gcttgaacac    2340
tagttttcga gcagttttag agatgatacc acttttacac tgttttttctc tgtaattta    2400 gttcctatg gttcctggta taaacatgta aaatcttggt gggaaaaggg aaagagtcca    2460
cgtgtactat ttcttttcta cgaagacctg aaagaggtga ggaactggga acacataagc    2520
aacttggtaa tttctaagat gttagcattt gaaaatactc tggatacaaa atattcctt    2580 taaataaatg atgacagcca tctcgtaaat ttttaaaagg aaaggaccaa aataatacag    2640
atactttagc atagatttga agctagcaaa taaaaatatt ctgaaaataa atacatttta    2700
aaccacaagt ctcaaaaatt tcaaagaaaa aatttgaaag aacttgactt catgaatcaa    2760
taacacacac acataggcac acacacacac acattcacac acaaggaatc aacatgggca    2820
agcaattaac tggtctgcaa atgtagagat gttgcaattg ttagataggt cctataaaat    2880
aaccatgctt aatatgttta aataaataaa agatgaaatt ttaaaaatta caaagaaaca    2940
aaaactatta aaattgacag agcagatttg aaaaaaaata gccaaataca atttctaaaa    3000
ataactaaaa aaatatgaaa aattaagaga tgggttcaat aatagattag acatggctac    3060
atagtgaatt attgaagtaa aagatggagc taaggaaatt ctatagaatg tagcacagtg    3120
agataaatag gctatttgat gaaaagtaat ggttcttact aagtattagc atttaaaaaa    3180
taa                                                                 3183
```

<210> SEQ ID NO 4
<211> LENGTH: 1641
<212> TYPE: DNA
<213> ORGANISM: Homo sapiens

<400> SEQUENCE: 4

```
agcaaaacag ggtcatctac ccaaaattag aatagccaag gatattatcc taaataagtt      60
```

-continued

| | |
|---|---|
| gataaataag ctgaaatcga aaaggcaaac tacaatttat tgagcagaga atttagaaac | 120 |
| agcatttgat tggcatagag agaaatgtgc acttgaatac acattgcggt tagtattgca | 180 |
| aatagttgca ctgagagata tagctgaata atggtgtata ttataggagt ggcacagata | 240 |
| tggggatgtt tgtagctatg gtgtacagac aactgatgtt gcattgtgag tatttgactt | 300 |
| tttacacctt tcttaatcct ttcttgtttc tttgtttctc actaattaca ccaataaatt | 360 |
| aggagaaaaa tgaaaattgc ctgtatatct ttatccccca aacttgattt ttcacagggg | 420 |
| actttaggtt ttgagtatga tgtttgtttt catagacaac atctattaag tgtgattatg | 480 |
| catcaaggac tacaataagc attcacaaac atctcattta gttttttgaa taatcttaaa | 540 |
| gtatcttttta taagcatttt atggatgagg aaaattatac ttaaaacagc ttttataaaa | 600 |
| ttcccccaat tagatttctc attagaaatc taattctaat atcagtagga gaaagagaa | 660 |
| aggtttattt tttctctttc atttagatag tgatttattc agttttagca atttagttct | 720 |
| caaaacattt tctctcccta ggatatcaga aaagaggtga taaaattgat acatttcctg | 780 |
| gaaaggaagc catcagagga gcttgtggac aggattatac atcatacttc gttccaagag | 840 |
| atgaagaaca atccatccac aaattacaca acactgccag acgaaattat gaaccagaaa | 900 |
| ttgtcgccct tcatgagaaa gggtgagaaa atgtggttt gcctcgatac tagaggaagt | 960 |
| cacaaggtga catggttata ggcaaaaatc tagtgaggta ttttaatgcc tatgaaccca | 1020 |
| gcttaagttt tcttcagcag tctttcatat ttgaatacac tctttaagtt acacttctat | 1080 |
| tacattgcaa ttacctgttg attatttatt atatgcatca tattatgtta aaataactag | 1140 |
| cagactcctc aatctcagca ttggaaatag tatcacactc tactagctgt aatttaccaa | 1200 |
| gcctatgtgc ctcagtgtta caacatgtat catatagttc ctttaagttc taaccagaaa | 1260 |
| ttccgcagaa agattttatt cctctctctt tttgagttga agaaataagt ttagaatagt | 1320 |
| ttgtcaacat ttttttaacaa gtggcaaaca cctttcaagg gtaagtggca aaaaatagaa | 1380 |
| attcaaatat agctctgttt agcaaaaaat atcaacatat aaggagaaaa aaattctatt | 1440 |
| tgaagggaaa catagcctga tgagatatag ccagttaaca aatttaaagg catgtaagat | 1500 |
| attcagatat tcagagcact gggacaccag tctatttata tatgaggaag cagaaacaaa | 1560 |
| cagaatagaa tcaaatcttg ctctttgaac catactgtca gtgagagtca gggaatttgt | 1620 |
| aaaataacaa acctgccact g | 1641 |

<210> SEQ ID NO 5
<211> LENGTH: 1750
<212> TYPE: DNA
<213> ORGANISM: Homo sapiens

<400> SEQUENCE: 5

| | |
|---|---|
| aaaaaaaaaa aagatgaatt ccttctgcaa ggtgagtgtt ggaagtatgt taaaaagcaa | 60 |
| aacaggaaaa gcctgctgga ctattataat tacccagatg agaaacactc tctggctggc | 120 |
| agtagcagaa gtgtttaaga ggcagtagat ataagaaag cctgaatata atgaattaga | 180 |
| tgttgtggtt aagagaataa cgtccaagct tatgtgtaga tacctggtgt tgactctaca | 240 |
| caggtcatta aaatgtaaat ggagaaaaca caatatgcta aggaataaaa tgaatttat | 300 |
| tttgaactaa ttgtatttgg aaaatttgga cattttcag gtggcaaaat catgtaggca | 360 |
| gttgtatata aagcataagt ctggattta gtgctatcag cattaagatg atatttaaca | 420 |
| ccttgagagt gggtaaaaca tggatcttat cctgggagcc ccaacagctg agatgaaact | 480 |

```
tcagaagaaa aataaagtaa atggcataag aagaaagaat cagagaatta aatttgttgt        540
ttttttaaac caattaggac aaatccatct ttgtaagccc aaaaaagtat atcattaaag        600
gtatacattt gattcctaaa attgagaatt acaagtataa tatttgatta ggtgttaatg        660
aaagtgatga aattagcaaa cctaatgatt cttttggaa gacttaatat ttattgagct         720
ttcttttttg ttacaggaat tacaggagac tggaaaaatc actttacagt agccctgaat        780
gaaaaatttg ataaacatta tgagcagcaa atgaaggaat ctacactgaa gtttcgaact        840
gagatctaag aaggtctttc tttacttaac atatctgata ttaaagatttt cttttcatta      900 ttctccactt tttcttattt tagattgcta gaaaagacat aatcatggat tatgttgaca       960
tttctttttt aaatttttgt ttaactttt tttttttttt ttgagacaga gtctcactct        1020
gttgcctagg ctggaggaca gtggcacaat catggctgat tgcagccttg acctccttga       1080
ctcaattgat cctcccatct cagcctccca gtagctagg actacagaca tgtgcaacca        1140
tgtttggcta atttttttaa tgttttttg tagagatgag gtcttattat attgtccagg        1200
ctggtcttga attcctgggc tcaagcttcc caagtagctg caacaacagg cacacaccac       1260
catgctcaac taatttttatt tctattttt gtatagacag gggcttgcta tagtgtccag      1320
gctggtctga aacccttgag ctcaagtgat cttcccacac cagcctccca aaatactggg       1380
attacaggct tgagcctcca tgcctggccc caggtaacat gtttattgag ctgtacatgc       1440
atatgagaaa taagaaactt ttttttccta ctatcatctc ttaaattttg gtttcttttt       1500
tcttttgctt cctcttcttc ttttctattt tttataaata tcatgcacaa ctataaccta      1560
tgggaatgat gtagtaaccc agattattca tcttgttaga gttgtattaa aaataaacaa       1620
gcatttcaaa ttatttttgt gattgatttt ccatttagta ggacattagt atataataaa      1680
aatggtgcat gaactttgaa gactctggaa gaaagaatga aataatatat aaatagggg        1740 cataactata                                                              1750

<210> SEQ ID NO 6
<211> LENGTH: 1046
<212> TYPE: DNA
<213> ORGANISM: Homo sapiens

<400> SEQUENCE: 6
agaagtggtt ctcatctttt tttgcagctt aagatctgcc ttggtatttg aagagatata        60
aactagatca atttctttca caggatcaac taaacagtgt accacaatga attctgaact       120
tgactattat gaaaagtttg aagaagtcca tgggattcta atgtataaag attttgtcaa       180
atattgggat aatgtggaag cgttccaggc aagaccagat gatcttgtca ttgccaccta       240
ccctaaatct ggtacaacct gggttagtga aattgtgtat atgatctata agagggtga        300 tgtggaaaag tgcaaagaag atgtaatttt taatcgaata cctttcctgg aatgcagaaa       360
agaaaacctc atgaatggag taaaacaatt agatgagatg aattctccta gaattgtgaa       420
gactcatttg ccacctgaac ttcttcctgc ctcattttgg gaaaaggatt gtaagataat       480
ctatctttgc cggaatgcaa aggatgtggc tgtttccttt tattattct ttctaatggt       540 ggctggtcat ccaaatcctg gatccttttcc agagtttgtg gagaaattca tgcaaggaca      600
ggttccttat ggttcctggt ataaacatgt aaaatcttgg tggaaaagg gaaagagtcc       660 acgtgtacta tttctttct acgaagacct gaaagaggat atcagaaaag aggtgataaa       720
attgatacat ttcctggaaa ggaagccatc agaggagctt gtggacagga ttatacatca      780
tacttcgttc caagagatga agaacaatcc atccacaaat tacacaacac tgccagacga      840
```

-continued

```
aattatgaac cagaaattgt cgcccttcat gagaaaggga attacaggag actggaaaaa    900
tcactttaca gtagccctga atgaaaaatt tgataaacat tatgagcagc aaatgaagga    960
atctacactg aagtttcgaa ctgagatcta agaaggtctt tctttactta acatatctga   1020
tattaaagat ttcttttcat tattca                                        1046
```

<210> SEQ ID NO 7
<211> LENGTH: 294
<212> TYPE: PRT
<213> ORGANISM: Homo sapiens

<400> SEQUENCE: 7

```
Met Asn Ser Glu Leu Asp Tyr Tyr Glu Lys Phe Glu Glu Val His Gly
 1               5                   10                  15

Ile Leu Met Tyr Lys Asp Phe Val Lys Tyr Trp Asp Asn Val Glu Ala
                20                  25                  30

Phe Gln Ala Arg Pro Asp Asp Leu Val Ile Ala Thr Tyr Pro Lys Ser
            35                  40                  45

Gly Thr Thr Trp Val Ser Glu Ile Val Tyr Met Ile Tyr Lys Glu Gly
        50                  55                  60

Asp Val Glu Lys Cys Lys Glu Asp Val Ile Phe Asn Arg Ile Pro Phe
65                  70                  75                  80

Leu Glu Cys Arg Lys Glu Asn Leu Met Asn Gly Val Lys Gln Leu Asp
                85                  90                  95

Glu Met Asn Ser Pro Arg Ile Val Lys Thr His Leu Pro Pro Glu Leu
            100                 105                 110

Leu Pro Ala Ser Phe Trp Glu Lys Asp Cys Lys Ile Ile Tyr Leu Cys
        115                 120                 125

Arg Asn Ala Lys Asp Val Ala Val Ser Phe Tyr Tyr Phe Phe Leu Met
    130                 135                 140

Val Ala Gly His Pro Asn Pro Gly Ser Phe Pro Glu Phe Val Glu Lys
145                 150                 155                 160

Phe Met Gln Gly Gln Val Pro Tyr Gly Ser Trp Tyr Lys His Val Lys
                165                 170                 175

Ser Trp Trp Glu Lys Gly Lys Ser Pro Arg Val Leu Phe Leu Phe Tyr
            180                 185                 190

Glu Asp Leu Lys Glu Asp Ile Arg Lys Glu Val Ile Lys Leu Ile His
        195                 200                 205

Phe Leu Glu Arg Lys Pro Ser Glu Glu Leu Val Asp Arg Ile Ile His
    210                 215                 220

His Thr Ser Phe Gln Glu Met Lys Asn Asn Pro Ser Thr Asn Tyr Thr
225                 230                 235                 240

Thr Leu Pro Asp Glu Ile Met Asn Gln Lys Leu Ser Pro Phe Met Arg
                245                 250                 255

Lys Gly Ile Thr Gly Asp Trp Lys Asn His Phe Thr Val Ala Leu Asn
            260                 265                 270

Glu Lys Phe Asp Lys His Tyr Glu Gln Gln Met Lys Glu Ser Thr Leu
        275                 280                 285

Lys Phe Arg Thr Glu Ile
    290
```

<210> SEQ ID NO 8
<211> LENGTH: 55
<212> TYPE: DNA
<213> ORGANISM: Artificial Sequence

```
<220> FEATURE:
<223> OTHER INFORMATION: Primer

<400> SEQUENCE: 8
tgtaaaacga cggccagtgc aggatatttc tacatctcca tgaatgaaca tgact        55

<210> SEQ ID NO 9
<211> LENGTH: 64
<212> TYPE: DNA
<213> ORGANISM: Artificial Sequence
<220> FEATURE:
<223> OTHER INFORMATION: Primer

<400> SEQUENCE: 9
caggaaacag ctatgaccgc ttcacatcat taattaacta agtatcaaa tcaagactttt    60 ggtc                                                                 64

<210> SEQ ID NO 10
<211> LENGTH: 56
<212> TYPE: DNA
<213> ORGANISM: Artificial Sequence
<220> FEATURE:
<223> OTHER INFORMATION: Primer

<400> SEQUENCE: 10
tgtaaaacga cggccagtct ctctagttac ccaaactatt tgatatgcaa ctttgc       56

<210> SEQ ID NO 11
<211> LENGTH: 53
<212> TYPE: DNA
<213> ORGANISM: Artificial Sequence
<220> FEATURE:
<223> OTHER INFORMATION: Primer

<400> SEQUENCE: 11
caggaaacag ctatgaccga gctacctttt ctatgtccat atccaaacta ccg          53

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
tgtaaaacga cggccagtat agaaaatatt tcctgagtct gtggctattc agacacc      57

<210> SEQ ID NO 13
<211> LENGTH: 56
<212> TYPE: DNA
<213> ORGANISM: Artificial Sequence
<220> FEATURE:
<223> OTHER INFORMATION: Primer

<400> SEQUENCE: 13
caggaaacag ctatgaccgc tgtcttatgt agaagacctg atactaattg ccattc       56

<210> SEQ ID NO 14
<211> LENGTH: 56
<212> TYPE: DNA
<213> ORGANISM: Artificial Sequence
<220> FEATURE:
<223> OTHER INFORMATION: Primer

<400> SEQUENCE: 14
```

-continued tgtaaaacga cggccagtta ggcatgcaat gcataataat tacaccatgg ggaatg    56

<210> SEQ ID NO 15
<211> LENGTH: 60
<212> TYPE: DNA
<213> ORGANISM: Artificial Sequence
<220> FEATURE:
<223> OTHER INFORMATION: Primer

<400> SEQUENCE: 15
caggaaacag ctatgacctg gcaaaagaca gagttggaat taaaatatag actctctgac    60

<210> SEQ ID NO 16
<211> LENGTH: 53
<212> TYPE: DNA
<213> ORGANISM: Artificial Sequence
<220> FEATURE:
<223> OTHER INFORMATION: Primer

<400> SEQUENCE: 16
tgtaaaacga cggccagtaa accactgtca cctcaggtta ttgaagatgt ctt    53

<210> SEQ ID NO 17
<211> LENGTH: 51
<212> TYPE: DNA
<213> ORGANISM: Artificial Sequence
<220> FEATURE:
<223> OTHER INFORMATION: Primer

<400> SEQUENCE: 17
caggaaacag ctatgaccat gcttgctctt aaacctccag gccccttag a    51

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
tgtaaaacga cggccagtca tgctttgcct ctcttgctgg agagaacct    49

<210> SEQ ID NO 19
<211> LENGTH: 63
<212> TYPE: DNA
<213> ORGANISM: Artificial Sequence
<220> FEATURE:
<223> OTHER INFORMATION: Primer

<400> SEQUENCE: 19
caggaaacag ctatgaccgc ttcaaatcta tgctaaagta tctgtattat tttggtcctt    60
tcc    63

<210> SEQ ID NO 20
<211> LENGTH: 64
<212> TYPE: DNA
<213> ORGANISM: Artificial Sequence
<220> FEATURE:
<223> OTHER INFORMATION: Primer

<400> SEQUENCE: 20
tgtaaaacga cggccagtca cagcttttat aaaattcccc caattagatt tctcattaga    60
aatc    64

<210> SEQ ID NO 21
<211> LENGTH: 58
<212> TYPE: DNA
<213> ORGANISM: Artificial Sequence
<220> FEATURE:
<223> OTHER INFORMATION: Primer

<400> SEQUENCE: 21
caggaaacag ctatgacctc aaatatgaaa gactgctgaa gaaaacttaa gctgggtt    58

<210> SEQ ID NO 22
<211> LENGTH: 59
<212> TYPE: DNA
<213> ORGANISM: Artificial Sequence
<220> FEATURE:
<223> OTHER INFORMATION: Primer

<400> SEQUENCE: 22
tgtaaaacga cggccagtca tctttgtaag cccccaaaag tatatcatta aaggtatac    59

<210> SEQ ID NO 23
<211> LENGTH: 62
<212> TYPE: DNA
<213> ORGANISM: Artificial Sequence
<220> FEATURE:
<223> OTHER INFORMATION: Primer

<400> SEQUENCE: 23
caggaaacag ctatgaccag ttaaacaaaa atttaaaaag aaaatgtcaa cataatccat    60
ga    62

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
tgtaaaacga cggccagtca gtgtaccaca atgaattctg    40

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25
caggaaacag ctatgacccc ttcttagatc tcagttcgaa    40

<210> SEQ ID NO 26
<211> LENGTH: 51
<212> TYPE: DNA
<213> ORGANISM: Artificial Sequence
<220> FEATURE:
<223> OTHER INFORMATION: Primer

<400> SEQUENCE: 26
tgtaaaacga cggccagtga ttctaatgta taaatatttt gtcaaatatt g    51

<210> SEQ ID NO 27
<211> LENGTH: 51
<212> TYPE: DNA
<213> ORGANISM: Artificial Sequence
<220> FEATURE:

-continued

```
<223> OTHER INFORMATION: Primer

<400> SEQUENCE: 27
caggaaacag ctatgaccca atatttgaca aaatatttat acattagaat c          51

<210> SEQ ID NO 28
<211> LENGTH: 47
<212> TYPE: DNA
<213> ORGANISM: Artificial Sequence
<220> FEATURE:
<223> OTHER INFORMATION: Primer

<400> SEQUENCE: 28
tgtaaaacga cggccagtgg ataatgtgga agtgttccag gcaagac               47

<210> SEQ ID NO 29
<211> LENGTH: 47
<212> TYPE: DNA
<213> ORGANISM: Artificial Sequence
<220> FEATURE:
<223> OTHER INFORMATION: Primer

<400> SEQUENCE: 29
caggaaacag ctatgaccgt cttgcctgga acacttccac attatcc               47

<210> SEQ ID NO 30
<211> LENGTH: 47
<212> TYPE: DNA
<213> ORGANISM: Artificial Sequence
<220> FEATURE:
<223> OTHER INFORMATION: Primer

<400> SEQUENCE: 30
tgtaaaacga cggccagtcc agaaattgtc gcacttcatg agaaagg               47

<210> SEQ ID NO 31
<211> LENGTH: 47
<212> TYPE: DNA
<213> ORGANISM: Artificial Sequence
<220> FEATURE:
<223> OTHER INFORMATION: Primer

<400> SEQUENCE: 31
caggaaacag ctatgacccc tttctcatga agtgcgacaa tttctgg               47
```

SULFOTRANSFERASE 1E1 SEQUENCE VARIANTS

CROSS-REFERENCE TO RELATED APPLICATIONS

This application is a divisional of U.S. Ser. No. 10/354,763, filed Jan. 30, 2003, which claims priority from U.S. Provisional Application Ser. No. 60/353,066, filed Jan. 30, 2002.

STATEMENT AS TO FEDERALLY SPONSORED RESEARCH

This invention was made with government support under grant numbers GM35720, GM61388, and awarded by the National Institutes of Health, and grant number DAMD17-99-1-9281, awarded by the Department of Defense. The government has certain rights in the invention.

TECHNICAL FIELD

The invention relates to sulfotransferase nucleic acid and amino acid sequence variants.

BACKGROUND

Sulfate conjugation, i.e., sulfonation, is an important pathway in the biotransformation of many neurotransmitters, hormones, drugs and other xenobiotics, and is catalyzed by cytosolic sulfotransferase enzymes designated "SULT." SULT enzymes are encoded by a gene superfamily, which in mammals is divided into two families: SULT1, or phenol SULTs, and SULT2, or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) subfamilies. SULT2 subfamilies include two hydroxysteroid SULTs, 2A1 and 2B1.

Members of the SULT1E subfamily catalyze the sulfate conjugation of estrogens. Human SULT1E1, for example, catalyzes the transfer of a sulfonate group from the sulfonate donor 3'-phosphoadenosine 5'-phosphosulfate (PAPS) to the hydroxyl group of an estrogen molecule. SULT1E1 is expressed in adult human liver, small intestine, adrenal cortex, adrenal medulla, mammary gland, ovary, endometrium, prostate, testis, and epididymus. It is also expressed in fetal lung, liver, and kidney.

SUMMARY

The invention is based on the discovery of sequence variants that occur in both coding and non-coding regions of SULT1E1 nucleic acids. Certain SULT1E1 nucleotide sequence variants encode SULT1E1 enzymes that are associated with individual differences in enzymatic activity. Other SULT1E1 sequence variants in non-coding regions of the SULT1E1 nucleic acid may alter regulation of transcription and/or splicing of the SULT1E1 nucleic acid. Discovery of these sequence variants allows individual differences in the sulfate conjugation of drugs and other xenobiotics in humans to be assessed such that particular treatment regimens can be tailored to an individual based on the presence or absence of one or more sequence variants. Identification of SULT1E1 sequence variants also allows predisposition to hormone dependent diseases or chemical carcinogenesis to be assessed in individuals.

In one aspect, the invention features an isolated nucleic acid molecule containing a SULT1E1 nucleic acid sequence, where the nucleic acid molecule is at least ten nucleotides in length, and where the SULT1E1 nucleic acid sequence contains a nucleotide sequence variant relative to SEQ ID NO:1, SEQ ID NO:2, SEQ ID NO:3, SEQ ID NO:4, SEQ ID NO:5, or SEQ ID NO:6. The nucleotide sequence variant can be at a position selected from the group consisting of position −232, −190, 64, 95, 237, 459, or 758 relative to the adenine of the SULT1E1 translation initiation codon. The nucleotide sequence variant relative to the adenine of the SULT1E1 translation initiation codon can be selected from the group consisting of an adenine substitution for guanine at position −232, a guanine substitution for cytosine at position −190, a thymine substitution for guanine at position 64, a thymine substitution for cytosine at position 95, a cytosine substitution for thymine at position 237, a thymine substitution for cytosine at position 459, and an adenine substitution for cytosine at position 758.

The nucleotide sequence variant can be at a position selected from the group consisting of position −20 relative to the guanine in the splice acceptor site of intron 1 (e.g., a thymine substitution for adenine); position 22 relative to the guanine in the splice donor site of intron 2 (e.g., a cytosine substitution for thymine); position −80 relative to the guanine in the splice acceptor site of intron 3 (e.g., a guanine substitution for adenine); and position 69 or 139 relative to the guanine in the splice donor site of intron 4 (e.g., a thymine substitution for adenine at position 69 or a thymine substitution for adenine at position 139). The nucleotide sequence variant can be at a position selected from the group consisting of position −23 relative to the guanine in the splice acceptor site of intron 4 (e.g., a guanine substitution for adenine); position 55 relative to the guanine in the splice donor site of intron 5 (e.g., a thymine substitution for cytosine); position 55 relative to the guanine in the splice donor site of intron 6 (e.g., a guanine deletion); position −39 relative to the guanine in the splice acceptor site of intron 6 (e.g., a cytosine substitution for thymine); and position −63 relative to the guanine in the splice acceptor site of intron 7 (e.g., a guanine substitution for thymine). The nucleotide sequence variant can be a substitution or a deletion.

In another aspect, the invention features an isolated nucleic acid encoding a SULT1E1 polypeptide, where the polypeptide contains a SULT1E1 amino acid sequence variant relative to the amino acid sequence of SEQ ID NO:7. The amino acid sequence variant can be at a residue selected from the group consisting of 22, 32, and 253.

The invention also features an isolated SULT1E1 polypeptide, wherein the polypeptide contains a SULT1E1 amino acid sequence variant relative to the amino acid sequence of SEQ ID NO:7. The amino acid sequence variant can be at a residue selected from the group consisting of 22, 32, and 253. The amino acid sequence variant at residue 22 can be tyrosine, the amino acid sequence variant at residue 32 can be valine, and the amino acid sequence variant at residue 253 can be histidine. The activity of the polypeptide can be altered relative to a wild type SULT1E1 polypeptide.

In another aspect, the invention features an article of manufacture containing a substrate, where the substrate contains a population of the isolated SULT1E1 nucleic acid molecules described above. The substrate can contain a plurality of discrete regions, where each region contains a different population of isolated SULT1E1 nucleic acid molecules, and where each population of molecules contains a different SULT1E1 nucleotide sequence variant.

In yet another aspect, the invention features a method for determining if a mammal is predisposed to cancer. The method can include: a) obtaining a biological sample from the mammal; and b) detecting the presence or absence of a SULT1E1 nucleotide sequence variant in the sample, where predisposition to cancer is determined based on the presence or absence of the variant. The method can further include detecting the presence or absence of a plurality of the SULT1E1 nucleotide sequence variants in the sample to obtain a variant profile of the mammal, where predisposition to cancer is determined based on the variant profile. The cancer can be an estrogen responsive cancer (e.g., breast cancer or endometrial cancer).

In another aspect, the invention features a method for assisting a medical or research professional. The method can include: a) obtaining a biological sample from a mammal; and b) detecting the presence or absence of a plurality of SULT1E1 nucleotide sequence variants in the sample to obtain a variant profile of the mammal. The method can further include communicating the profile to a medical or research professional.

In another aspect, the invention features an isolated nucleic acid molecule containing a SULT1E1 nucleic acid sequence, where the nucleic acid molecule is at least ten nucleotides in length, and where the SULT1E1 nucleic acid sequence contains at least two nucleotide sequence variants relative to SEQ ID NO:1, SEQ ID NO:2, SEQ ID NO:3, SEQ ID NO:4, SEQ ID NO:5, or SEQ ID NO:6. The nucleotide sequence variant can be at a position selected from the group consisting of: a) position −232, −190, −64, 64, 95, 237, 459, or 758 relative to the adenine of the SULT1E1 translation initiation codon; b) position 69 relative to the splice donor site of intron 1; c) position −73 or −20 relative to the guanine in the splice acceptor site of intron 1; d) position 22 relative to the guanine in the splice donor site of intron 2; e) position −137 or −80 relative to the guanine in the splice acceptor site of intron 3; f) position 69 or 139 relative to the guanine in the splice donor site of intron 4; g) position −23 relative to the guanine in the splice acceptor site of intron 4; h) position 55 relative to the guanine in the splice donor site of intron 5; i) position −10 relative to the guanine in the splice acceptor site of intron 5; j) position 55 relative to the guanine in the splice donor site of intron 6; k) position −39 relative to the guanine in the splice acceptor site of intron 6; and l) position −121 or −63 relative to the guanine in the splice acceptor site of intron 7.

In still another aspect, the invention features an isolated nucleic acid molecule containing a SULT1E1 nucleic acid sequence, where the nucleic acid molecule is at least ten nucleotides in length, and wherein the SULT1E1 nucleic acid sequence has at least 99% sequence identity to a region of SEQ ID NO:6. Nucleotide 64 relative to the adenine of the SULT1E1 translation initiation codon can be a thymine, nucleotide 95 relative to the adenine of the SULT1E1 translation initiation codon can be a thymine, or nucleotide 758 relative to the adenine of the SULT1E1 translation initiation codon can be an adenine. The region can be selected from the group consisting of: a) nucleotides 1 to 100 of SEQ ID NO:6 relative to the adenine of the SULT1E1 translation initiation codon; b) nucleotides 50 to 150 of SEQ ID NO:6 relative to the adenine of the SULT1E1 translation initiation codon; and c) nucleotides 700 to 800 of SEQ ID NO:6 relative to the adenine of the SULT1E1 translation initiation codon.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the genomic sequence of the reference human SULT1E1 (SEQ ID NOS:1-5). Intron, 5'-flanking region and 3'-flanking region sequences are in lower case letters. Primers used for resequencing are underlined. Single nucleotide polymorphisms (SNPs) are bold, in italics, and are underlined. The position and nature of each SNP, insertion, and deletion is indicated proximal to the markings described. Exon sequences are bolded and in upper case letters. The start codon also is italicized.

FIGS. 2A and 2B are the cDNA and amino acid sequences of the reference SULT1E1, respectively (SEQ ID NOS:6 and 7). Start and stop codons are bold and underlined.

DETAILED DESCRIPTION

Figure 3:
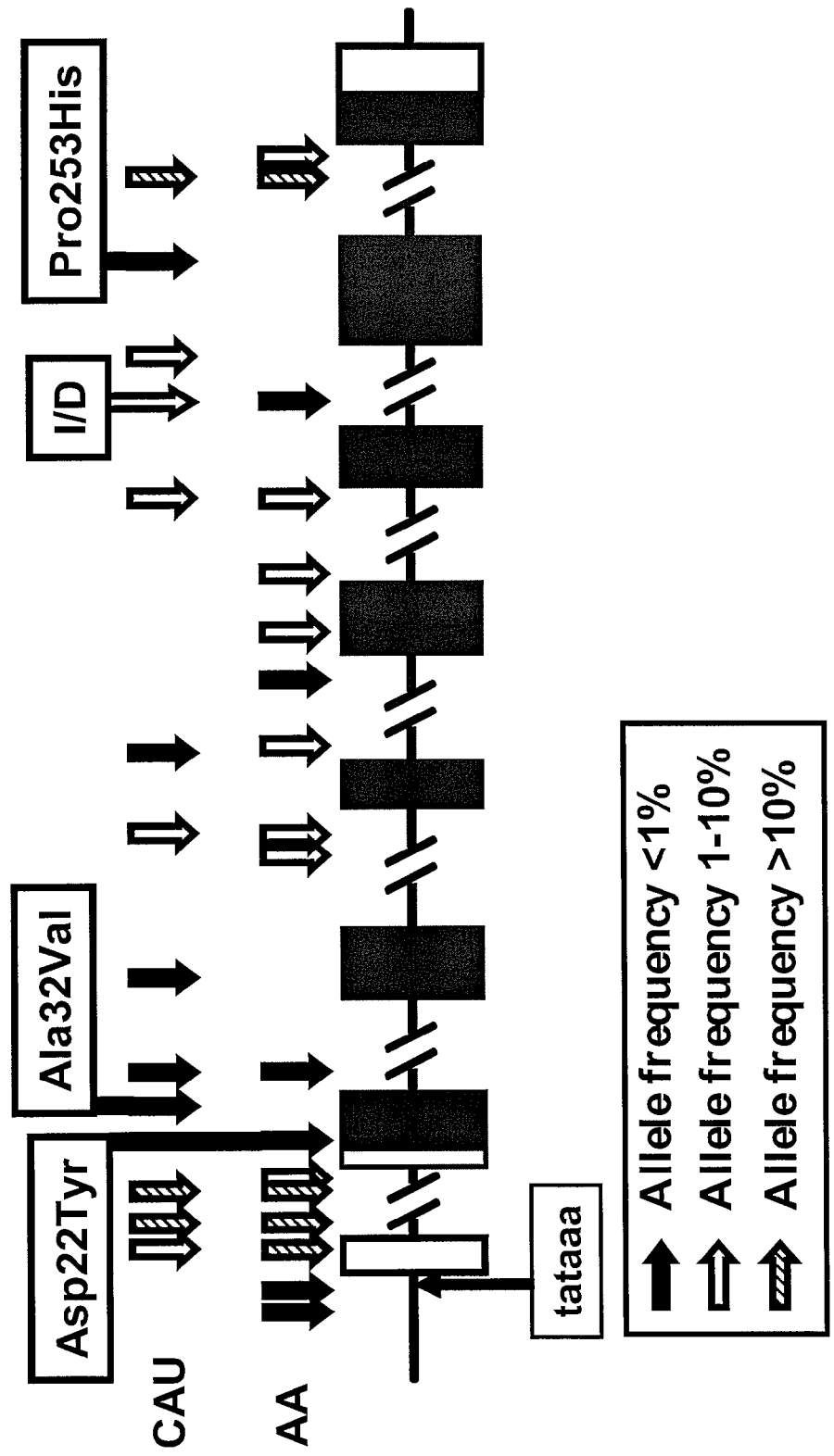
FIG. 3 is a schematic showing locations of polymorphisms within the SULT1E1 sequence.

The invention features SULT1E1 nucleotide and amino acid sequence variants. SULT1E1 catalyzes the transfer of a sulfonate group to steroid hormone molecules such as estrone, estradiol, catecholestrogens, and methoxyestradiol. For example, SULT1E1 can catalyze the transfer of a sulfonate group from PAPS to estradiol to form estradiol 3-O-sulfate. Sulfonation inactivates estrogen molecules, as sulfonated estrogens have no effect on the estrogen receptor. Therefore, increased sulfonation of estrogens may be a protective mechanism against estrogen responsive cancers such as breast cancer and endometrial cancer. SULT1E1 has been shown to modulate local estrogen levels in a breast cancer cell line. Without being bound by a particular mechanism, a loss or down-regulation of SULT1E1 could increase the growth stimulating effect of estrogen and contribute to the process of tumor initiation and promotion in breast epithelium. Thus, detecting sulfotransferase nucleic acid and amino acid sequence variants can be useful for diagnosing cancer as well as for determining a predisposition for cancer.

Furthermore, sulfation can detoxify compounds, as the resulting ionized, organic sulfates are more readily excreted than unsulfated compounds. Thus, detecting sulfotransferase nucleic acid and amino acid sequence variants can facilitate the prediction of therapeutic efficacy and toxicity of drugs on an individual basis, as well as the ability to biotransform certain hormones and neurotransmitters.

Nucleic Acid Molecules

The invention features isolated nucleic acids that include a SULT1E1 nucleic acid sequence. The SULT1E1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-SULT1E1 proteins). The term "isolated" as used herein with respect to nucleic acids also includes any non-naturally-occurring nucleic acid sequence since non-naturally-occurring sequences are not found in nature and do not have immediately contiguous sequences in a naturally-occurring genome.

An isolated nucleic acid can be, for example, a DNA molecule, provided one or both of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, a nucleic acid can be about 8, 9, 10-20 (e.g., 11, 12, 13, 14, 15, 16, 17, 18, 19, or 20 nucleotides in length), 20-50, 50-100, or greater than 100 nucleotides in length (e.g., greater than 150, 200, 250, 300, 350, 400, 450, 500, 750, or 1000 nucleotides in length). Nucleic acids of the invention can be in a sense or an antisense orientation, can be complementary to the SULT1E1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2'-hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in the SULT1E1 reference sequence, and includes variations that occur in coding and non-coding regions, including exons, introns, and untranslated sequences. Nucleotides are referred to herein by the standard one-letter designation (A, C, G, or T). Variations can include single nucleotide substitutions, deletions of one or more nucleotides, and insertions of one or more nucleotides. Reference SULT1E1 nucleic acid sequences are provided in FIG. 1 (SEQ ID NOS: 1-5) and in GenBank (Accession Nos: U20515-U20521). The reference SULT1E1 messenger RNA (mRNA) including the reference SULT1E1 cDNA is provided in FIG. 2A (SEQ ID NO:6) and in GenBank (Accession No: U08098), and the corresponding SULT1E1 amino acid sequence is provided in FIG. 2B (SEQ ID NO:7) and in GenBank (Accession No. U08098). The nucleic acid and amino acid reference sequences also are referred to herein as "wild type."

As used herein, "untranslated sequence" includes 5'- and 3'-flanking regions that are outside of the mRNA as well as 5'- and 3'-untranslated regions (5'-UTR or 3'-UTR) that are part of the mRNA, but are not translated. Positions of nucleotide sequence variants in 5'-untranslated sequences are designated as "−X" relative to the "A" in the translation initiation codon; positions of nucleotide sequence variants in the coding sequence and 3'-untranslated sequence are designated as "+X" or "X" relative to the "A" in the translation initiation codon. Nucleotide sequence variants that occur in introns are designated as "+X" or "X" relative to "G" in the splice donor site (GT) or as "−X" relative to the "G" in the splice acceptor site (AG).

In some embodiments, a SULT1E1 nucleotide sequence variant encodes a SULT1E1 polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-300 residues, or a full-length SULT1E1 polypeptide). SULT1E1 polypeptides may or may not have sulfotransferase catalytic activity, or may have altered activity relative to the reference SULT1E1 polypeptide. Polypeptides that do not have activity or have altered activity can be useful for diagnostic purposes (e.g., for producing antibodies having specific binding affinity for variant sulfotransferase polypeptides).

Corresponding SULT1E1 polypeptides, irrespective of length, that differ in amino acid sequence from the reference SULT1E1 polypeptide are referred to herein as allozymes. For example, a SULT1E1 nucleic acid sequence that includes a thymine at nucleotide 64 relative to the adenine in the SULT1E1 translation initiation site encodes a SULT1E1 polypeptide having a tyrosine at amino acid residue 22. This polypeptide (Asp22Tyr) would be considered an allozyme with respect to the reference SULT1E1 polypeptide that contains an aspartic acid at amino acid residue 22. Additional non-limiting examples of SULT1E1 sequence variants that alter amino acid sequence include variants at nucleotides 95 and 758 relative to the adenine in the SULT1E1 translation initiation site. For example, a SULT1E1 nucleic acid molecule can include a thyrnine at nucleotide 95 and encode a SULT1E1 polypeptide having a valine residue at amino acid 32 in place of an alanine residue (Ala32Val), or can have an adenine at nucleotide 758 and encode a SULT1E1 polypeptide having a histidine at amino acid 253 in place of a proline (Pro253His). In addition, a SULT1E1 nucleic acid can encode an allozyme having two or more amino acid variants, e.g., the nucleic acid can encode a polypeptide having two or more amino acid changes at residues 22, 32, and 253.

SULT1E1 allozymes as described above are encoded by a series of sulfotransferase alleles. These alleles represent nucleic acid sequences containing sequence variants, typically multiple sequence variants, within coding and non-coding sequences. Representative examples of single nucleotide variants are described above. Table 2 includes three polymorphisms that result in SULT1E1 alleles encoding the SULT1E1 allozymes Asp22Tyr, Ala32Val, and Pro253H is. The number of alleles and allozymes for SULT1E1 indicates the potential complexity of SULT pharmacogenetics. Such complexity emphasizes the need for determining single nucleotide variants, (i.e., single nucleotide polymorphisms, SNPs) as well as complete haplotypes (i.e., the set of alleles on one chromosome or a part of a chromosome) of patients. See Table 4 for haplotypes of SULT1E1.

Certain SULT1E1 nucleotide sequence variants do not alter the amino acid sequence. Such variants, however, could alter regulation of transcription as well as mRNA stability. SULT1E1 variants can occur in intron sequences, for example, within intron 1, 2, 3, 4, 5, 6, or 7. In particular, the nucleotide sequence variant can include a guanine substitution at nucleotide 69, a cytosine substitution at nucleotide −73, or a thymine substitution at nucleotide −20 of intron 1. Intron 2 variants can include a cytosine substitution at nucleotide 22. Intron 3 variants can include a guanine substitution at nucleotide −137 or nucleotide −80. Intron 4 variants can include a thymine substitution at nucleotide 69 or nucleotide 139, or a guanine substitution at nucleotide −23. Intron 5 sequence variants can include a thymine substitution at nucleotide 55 or a guanine substitution at nucleotide −10. Intron 6 sequence variants can include a guanine deletion at nucleotide 55 or a cytosine substitution at nucleotide −39. Intron 7 variants can include a thymine substitution at nucleotide −121 or a guanine substitution at nucleotide-63.

SULT1E1 nucleotide sequence variants that do not change the amino acid sequence also can be within an exon or in 5'- or 3'-untranslated sequences. For example, a nucleotide sequence variant can include an adenine substitution at nucleotide-64 of exon 1, a cytosine substitution at nucleotide 237 of exon 3, or a thymine substitution at nucleotide 459 of exon 5. In addition, the 5'-flanking region of SULT1E1 can include an adenine substitution at nucleotide −232 or a guanine substitution at nucleotide-190 relative to the adenine in the SULT1E1 transcription initiation site. Nucleotides −232 and −190 are at positions 643 and 685, respectively, relative to the first nucleotide of SEQ ID NO:1 (see FIG. 1).

Isolated nucleic acid molecules provided herein can contain a SULT1E1 nucleic acid sequence that is at least ten nucleotides in length and includes a nucleotide sequence variant relative to SEQ ID NO:1, SEQ ID NO:2, SEQ ID NO:3, SEQ ID NO:4, SEQ ID NO:5, or SEQ ID NO:6. In some embodiments, a SULT1E1 nucleic acid can include at least two (e.g., two, three, four, five, or more than five) nucleotide sequence variants. Examples of SULT1E1 nucleotide sequence variants are provided herein.

In some embodiments, nucleic acid molecules of the invention can have at least 97% (e.g., 97.5%, 98%, 98.5%, 99.0%, 99.5%, 99.6%, 99.7%, 99.8%, 99.9%, or 100%) sequence identity with a region of SEQ ID NO: 1, SEQ ID NO:2, SEQ ID NO:3, SEQ ID NO:4, SEQ ID NO:5, or SEQ ID NO:6 that includes one or more variants described herein. The region of SEQ ID NO:1, 2, 3, 4, 5, or 6 is at least ten nucleotides in length (e.g., ten, 15, 20, 50, 60, 70, 75, 100, 150 or more nucleotides in length). For example, a nucleic acid molecule can have at least 99% identity with a region of SEQ ID NO:6 containing nucleotides −100 to −1, 1 to 100, 50 to 150, 200 to 300, 400 to 500, or 700 to 800 relative to the adenine of the SULT1E1 translation initiation codon, where the nucleotide sequence of SEQ ID NO:6 includes one or more of the variants described herein. For example, the nucleotide sequence of SEQ ID NO:6 can have, with respect to the adenine of the SULT1E1 translation initiation site, an adenine at position−69, a thymine at position 64, a thymine at position 95, a cytosine at position 237, a thymine at position 459, or an adenine at position 758, and combinations thereof.

In another embodiment, a nucleic acid molecule can have at least 99% identity with a region of SEQ ID NO:1 containing nucleotides −275 to −175 or −250 to −150 relative to the adenine of the SULT1E1 translation initiation codon, nucleotides 1 to 100 relative to the guanine in the splice donor site of intron 1, nucleotides −125 to −25 or −100 to −1 relative to the guanine in the splice acceptor site of intron 1, or nucleotides 1 to 100 relative to the guanine in the splice donor site of intron 2, where the nucleotide sequence of SEQ ID NO: 1 includes one or more of the variants described herein. For example, the nucleotide sequence of SEQ ID NO: 1 can have an adenine at position −232 relative to the adenine of the SULT1E1 translation initiation site (position 643 of SEQ ID NO: 1), a guanine at position −190 relative to the adenine of the SULT1E1 translation initiation site (position 685 of SEQ ID NO:1), a guanine at position 69 relative to the guanine of the splice donor site of intron 1, a cytosine at position −73 relative to the guanine in the splice acceptor site of intron 1, a thymine at position −20 relative to the guanine in the splice acceptor site of intron 1, or a cytosine at position 22 relative to the guanine in the splice donor site of intron 2, and combinations thereof.

In another embodiment, a nucleic acid molecule can have at least 99% identity with a region of SEQ ID NO:2 containing nucleotides −175 to −75 or −125 to −25 relative to the guanine in the splice acceptor site of intron 3 or nucleotides 1 to 100 or 75 to 175 relative to the guanine in the splice donor site of intron 4, where the nucleotide sequence of SEQ ID NO:2 includes one or more of the variants described herein. For example, the nucleotide sequence of SEQ ID NO:2 can have a guanine at nucleotide −137 or at nucleotide −80 relative to the guanine of the splice acceptor site of intron 3 or a thymine at position 69 or 139 relative to the guanine in the splice donor site of intron 4, and combinations thereof.

In still another embodiment, a nucleic acid molecule can have at least 99% identity with a region of SEQ ID NO:3 containing nucleotides −100 to −1 relative to the guanine in the splice acceptor site of intron 4, nucleotides 1 to 100 relative to the guanine in the splice donor site of intron 5, nucleotides −100 to −1 relative to the guanine in the splice acceptor site of intron 5, or nucleotides 1 to 100 relative to the guanine in the splice donor site of intron 6, where the nucleotide sequence of SEQ ID NO:3 includes one or more of the variants described herein. For example, the nucleotide sequence of SEQ ID NO:3 can have a guanine at nucleotide −23 relative to the guanine in the splice acceptor site of intron 4, a thymine at nucleotide 55 relative to the guanine in the splice donor site of intron 5, a guanine at position −10 relative to the guanine in the splice acceptor site of intron 5, or a deletion at position 55 relative to the guanine in the splice donor site of intron 6, and combinations thereof.

A nucleic acid molecule also can have at least 99% identity with a region of SEQ ID NO:4 containing nucleotides −100 to −1 relative to the guanine in the splice acceptor site of intron 6, where the nucleotide sequence of SEQ ID NO:4 includes one or more of the variants described herein. For example, the nucleotide sequence of SEQ ID NO:4 can have a cytosine at nucleotide −39 relative to the guanine in the splice acceptor site of intron 6. In another embodiment, a nucleic acid molecule can have at least 99% identity with a region of SEQ ID NO:5 containing nucleotides −175 to −125 or nucleotides −100 to −1 relative to the guanine in the splice acceptor site of intron 7, where the nucleotide sequence of SEQ ID NO:5 includes one or more of the variants described herein. For example, the nucleotide sequence of SEQ ID NO:5 can have a thymine at nucleotide −121 relative to the guanine in the splice acceptor site of intron 7 or a guanine at nucleotide −63 relative to the guanine in the splice acceptor site of intron 7, or combinations thereof.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at fr.com/blast) or the U.S. government's National Center for Biotechnology Information web site (www.ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:6, (2) the Bl2seq program presents 900 nucleotides from the target sequence aligned with a region of the sequence set forth in SEQ ID NO: 1 where the first and last nucleotides of that 900 nucleotide region are matches, and (3) the number of matches over those 900 aligned nucleotides is 850, then the 1000 nucleotide target sequence contains a length of 900 and a percent identity over that length of 94 (i.e., 850 900×100=94).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a SULT1E1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA*, 87:1874-1878; and Weiss (1991) Science 254:1292.

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIG. 1 can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, ed. Ausubel et al., 1992. Examples of positions that can be modified include those described herein.

SULT1E1 Polypeptides

Isolated SULT1E1 polypeptides of the invention include an amino acid sequence variant relative to the reference SULT1E1 polypeptide (FIG. 2B; SEQ ID NO:7; GenBank Accession No. U08098). The term "isolated" with respect to a SULT1E1 polypeptide refers to a polypeptide that has been separated from cellular components that naturally accompany it. Typically, the polypeptide is isolated when it is at least 60% (e.g., 70%, 80%, 90%, 95%, or 99%), by weight, free from proteins and naturally occurring organic molecules that are naturally associated with it. In general, an isolated polypeptide will yield a single major band on a non-reducing polyacrylamide gel.

SULT1E1 polypeptides of the invention include variants at one or more of residues 22, 32, and 253. In particular, a tyrosine residue can be substituted at position 22, a valine residue at position 32, or a histidine at position 253. SULT1E1 polypeptides may have more than one amino acid substitution.

In some embodiments, the activity of SULT1E1 allozymes can be altered relative to the reference SULT1E1 polypeptide. As described herein, certain SULT1E1 allozymes have reduced activity (e.g., Asp22Tyr and Ala32Val). In other embodiments, the activity of SULT1E1 allozymes (e.g., Pro253His) have activity that is similar to that of the reference SULT1E1 polypeptide. The activity of SULT1E1 polypeptides can be measured as described by Foldes and Meek (*Biochim. Biophys. Acta,* 327:365-374, 1973) or Hernandez et al. (*Drug Metab. Disposit.* 20:413-422, 1992). Briefly, SULT1E1 activity can be assayed in vitro using a sulfate acceptor substrate such as 17-β estradiol (E2, Sigma Chemical Co., St. Louis, Mo.) and a donor sulfate molecule such as PAPS. In general, recombinant SULT1E1 polypeptides can be incubated at 37° C. with 0.05 µM of sulfate acceptor substrate and 0.4 µM labeled PAPS (e.g., $^{35}$S-PAPS from New England Nuclear Life Science Products, Inc., Boston Mass.). Reactions can be stopped by precipitating unreacted PAPS and SULT1E1 polypeptide (e.g., with barium hydroxide, barium acetate, and zinc sulfate). After centrifugation of the reaction mixture, radioactivity in the supernatant can be assessed. SULT1E1 activity can be expressed as nmole of sulfate conjugated product formed per hour of incubation. See Campbell et al. (1987) *Biochem. Pharmacol.* 36:1435-1446.

Other biochemical properties of allozymes, such as apparent $K_m$ values, also can be altered relative to the reference SULT1E1. Apparent $K_m$ values can be calculated, for example, by using the method of Wilkinson with a computer program written by Cleland. Wilkinson (1961) *Biochem. J.* 80:324-332 and Cleland (1963) *Nature* 198:463-365. As described herein, the apparent $K_m$ values for PAPS varied more than 3-fold among the allozymes tested (Asp22Tyr, Ala32Val, and Pro253His).

Isolated polypeptides of the invention can be obtained, for example, by extraction from a natural source (e.g., liver tissue), chemical synthesis, or by recombinant production in a host cell. To recombinantly produce SULT1E1 polypeptides, a nucleic acid sequence encoding a sulfotransferase variant polypeptide can be ligated into an expression vector and used to transform a bacterial or eukaryotic host cell (e.g., insect, yeast, or mammalian cells). In general, nucleic acid constructs include a regulatory sequence operably linked to a sulfotransferase nucleic acid sequence. Regulatory sequences do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express sulfotransferase variant polypeptides. A nucleic acid encoding a polypeptide of the invention can be cloned into, for example, a baculoviral vector such as pBlueBac (Invitrogen, San Diego, Calif.) and then used to co-transfect insect cells such as *Spodoptera frugiperda* (Sf9) cells with wild type DNA from *Autographa californica* multi-nuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Mammalian cell lines that stably express sulfotransferase variant polypeptides can be produced by using expression vectors with the appropriate control elements and a selectable marker. For example, the eukaryotic expression vector pCR3.1 (Invitrogen, San Diego, Calif.) and p91023(B) are suitable for expression of sulfotransferase variant polypeptides in mammalian cells such as Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable method, stable cell lines are selected, e.g., by antibiotic resistance to G418, kanamycin, or hygromycin. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

SULT1E1 variant polypeptides can be purified by known chromatographic methods including DEAE ion exchange, gel filtration, and hydroxylapatite chromatography. See, Van Loon and Weinshilboum (1990) *Drug Metab. Dispos.* 18:632-638; and Van Loon et al. (1992) *Biochem. Pharmacol.* 44:775-785. SULT1E1 polypeptides can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase. Immunoaffinity chromatography also can be used to purify SULT1E1 polypeptides.

Non-Human Mammals

The invention features non-human mammals that include SULT1E1 nucleic acids of the invention, as well as progeny and cells of such non-human mammals. Non-human mammals include, for example, rodents such as rats, guinea pigs, and mice, and farm animals such as pigs, sheep, goats, horses and cattle. Non-human mammals of the invention can express a SULT1E1 variant nucleic acid in addition to an endogenous SULT1E1 (e.g., a transgenic non-human that includes a SULT1E1 nucleic acid randomly integrated into the genome of the non-human mammal). Alternatively, an endogenous SULT1E1 nucleic acid can be replaced by a SULT1E1 variant nucleic acid of the invention through homologous recombination. See Shastry (1998) *Mol. Cell. Biochem.* 181:163-179, for a review of gene targeting technology.

In one embodiment, non-human mammals are produced that lack an endogenous SULT1E1 nucleic acid (i.e., a knockout), then a SULT1E1 variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous SULT1E1 nucleic acid. That is, cultured ES cells can be transformed with a knockout construct and cells selected in which the SULT1E1 gene is inactivated.

Nucleic acid constructs can be introduced into ES cells by, for example, electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual*, second edition, Cold Spring Harbor Press, Plainview, N.Y., 1989.

To generate a knockout animal, ES cells having at least one inactivated SULT1E1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated SULT1E1 allele. If the original ES cell was heterozygous for the inactivated SULT1E1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are "totipotent," i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the SULT1E1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated SULT1E1 gene, and then fused with enucleated oocytes. After activation of the oocytes, the eggs are cultured to the blastocyst stage, and implanted into a recipient. See Cibelli et al. (1998) *Science* 280:1256-1258. Adult somatic cells, including, for example, cumulus cells and mammary cells, can be used to produce animals such as mice and sheep, respectively. See, for example, Wakayama et al. (1998) *Nature* 394:369-374; and Wilmut et al. (1997) *Nature* 385: 810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. See, Wakayama et al. (1998) supra.

Non-human mammals of the invention such as mice can be used to screen, for example, toxicity of compounds that are substrates for SULT1E1, drugs that alter SULT1E1 activity, or for carcinogenesis. For example, SULT1E1 activity or toxicity can be assessed in a first group of such non-human mammals in the presence of a compound, and compared with SULT1E1 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally and parenterally. For example, the compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols. Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Detecting Sulfotransferase Sequence Variants

Sulfotransferase nucleotide sequence variants can be detected by, for example, sequencing exons, introns, 5'-untranslated sequences, or 3'-untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC; Underhill et al. (1997) *Genome Res.* 7:996-1005), infrared matrix-assisted laser desorption/ionization (IR-MALDI) mass spectrometry (WO 99/57318), and combinations of such methods. Genomic DNA generally is used in the analysis of sulfotransferase nucleotide sequence variants. Genomic DNA typically is extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.) and the A.S.A.P.™ Genomic DNA isolation kit (Boehringer Mannheim, Indianapolis, Ind.).

Typically, an amplification step is performed before proceeding with the detection method. For example, exons or introns of the sulfotransferase gene can be amplified then directly sequenced. Dye primer sequencing can be used to increase the accuracy of detecting heterozygous samples.

Allele specific hybridization also can be used to detect sequence variants, including complete haplotypes of a mammal. See, Stoneking et al. (1991) *Am. J. Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5'-end of reverse primer) and the resulting biotinylated amplification product is immobilized on an avidin or streptavidin coated substrate. Allele-specific restriction digests can be performed in the following manner. For nucleotide sequence variants that introduce a restriction site, restriction digest with the particular restriction enzyme can differentiate the alleles. For SULT1E1 sequence variants that do not alter a common restriction site, mutagenic primers can be designed that introduce a restriction site when the variant allele is present or when the wild type allele is present. A portion of SULT1E1 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The nucleotide insertion or deletion can be assessed by amplifying the region encompassing the variant. The size of the amplified products can be determined by comparison with size standards. For example, a region of SULT1E1 containing the deletion in intron 6 of can be amplified using a primer set from either side of the variant. One of the primers typically is labeled with, for example, a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See Myakishev et al. (2001) *Genome* 11:163-169.

Mismatch cleavage methods also can be used to detect differing sequences by PCR amplification, followed by hybridization with the wild type sequence and cleavage at points of mismatch. Chemical reagents such as carbodiimide or hydroxylamine and osmium tetroxide can be used to modify mismatched nucleotides to facilitate cleavage. Alternatively, SULT1E1 polypeptide variants can be detected using antibodies that have specific binding affinity for SULT1E1 allozymes. Variant SULT1E1 polypeptides can be produced in a number of ways, including recombinantly, as discussed above. Host animals such as rabbits, chickens, mice, guinea pigs, and rats can be immunized by injection of a SULT1E1 variant polypeptide. Adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a sulfotransferase variant polypeptide and standard hybridoma technology. In particular, monoclonal antibodies can be obtained by any technique that provides for the production of antibody molecules by continuous cell lines in culture such as described by Kohler et al. (1975) Nature 256:495, the human B-cell hybridoma technique (Kosbor et al. (1983) Immunology Today 4:72; Cole et al. (1983) Proc. Natl. Acad. Sci. USA 80:2026), and the EBV-hybridoma technique (Cole et al. (1983) Monoclonal Antibodies and Cancer Therapy, Alan R. Liss, Inc., pp. 77-96. Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a SULT1E1 variant polypeptide can be generated by known techniques. Such fragments include, but are not limited to, F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al. (1989) Science 246:1275. Once produced, antibodies or fragments thereof are tested for recognition of sulfotransferase variant polypeptides by standard immunoassay methods including ELISA techniques, radioimmunoassays, and Western blotting. See, Short Protocols in Molecular Biology, Chapter 11, Green Publishing Associates and John Wiley & Sons, Edited by Ausubel et al., 1992.

Methods

As a result of the present invention, it is now possible to determine the sulfonator status of a mammal (e.g., a human subject) as well as to determine if particular SNPs are linked to a particular disease or clinical condition. In some embodiments, for example, it is possible to determine whether a mammal is predisposed (i.e., has a relative greater risk) to a disease such as cancer (e.g., an estrogen responsive cancer). "Sulfonator status" refers to the ability of a mammal to transfer a sulfate group to a substrate. The presence of SULT1E1 allozymes with reduced activity may indicate a relatively increased risk for development of estrogen responsive cancers such as breast cancer or ovarian cancer. Additional risk factors including, for example, family history and other genetic factors can be considered when determining risk.

Sulfonator status or predisposition to cancer can be determined based on the presence or absence of a single SULT1E1 sequence variant or based on a variant profile. "Variant profile" refers to the presence or absence of a plurality (i.e., two or more sequence variants) of SULT1E1 nucleotide sequence variants or SULT1E1 amino acid sequence variants. For example, a variant profile can include the complete SULT1E1 haplotype of the mammal or can include the presence or absence of a set of common non-synonymous SNPs (i.e., single nucleotide substitutions that alter the amino acid sequence of a SULT1E1 polypeptide). Non-limiting examples of SULT1E1 haplotypes (haplotypes *1A-*1L, *2, *3, and *4) are found in Table 4. In one embodiment, the variant profile includes detecting the presence or absence of two or more non-synonymous SNPs (e.g., 2, 3, 4, 5, 6, or 7 non-synonymous SNPs and combinations thereof) described above. There may be ethnic-specific pharmacogenetic variation, as certain of the nucleotide and amino acid sequence variants described herein were detected solely in a particular ethnic group (i.e., a group of African-American subjects or a group of Caucasian subjects). In addition, the variant profile can include detecting the presence or absence of any type of SULT1E1 SNP together with any other SULT1E1 SNP (i.e., a polymorphism pair or groups of polymorphism pairs). Such polymorphism pairs include, without limitation, those pairs described in Table 3. Furthermore, the variant profile can include detecting the presence or absence of any SULT1E1 SNP together with any SNP from another SULT nucleic acid.

Articles of Manufacture

The invention provides articles of manufacture that contain populations of isolated SULT1E1 nucleic acid molecules or SULT1E1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different SULT1E1 nucleic acid or SULT1E1 polypeptide sequence variant. Such articles of manufacture can include two or more SULT1E1 sequence variants, or can include all of the sequence variants known for SULT1E1. Furthermore, nucleic acid molecules containing sequence variants for other sulfotransferases, such as SULT1A1, SULT1A2, or SULT1A3, can be included on the substrate. See, WO 99/64630 and WO 00/20605 for a description of other SULT1A1, SULT1A2, and SULT1A3 sequence variants.

Suitable substrates can be of any shape or form and can be constructed from, for example, glass, silicon, metal, plastic, cellulose or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al. (1996) Nature Genet. 14:441-447; and U.S. Pat. Nos. 5,770,722 and 5,733,729.

EXAMPLES

Example 1

PCR Amplification and DNA Sequencing

60 African American and 60 Caucasian genomic DNA samples were obtained from the Coriell Cell Repository (Coriell Institute for Medical Research, Camden, N.J.). Specifically, 60 genomic DNA samples each from the two 100 item sample sets HD100AA and HD100CAU were used to as templates in PCR with SULT1E1-specific primers. All DNA samples had been anonymized by the National Institutes of Health prior to their deposit in the Coriell Cell Repository. To make it possible to sequence SULT1E1, the eight exons in the gene were amplified from each of the 120 DNA samples by use of PCR. Specifically, PCR primers were designed that flanked the exons and that would produce amplification products 400-500 base pairs in length. Therefore, eight separate amplifications were performed for each DNA sample.

Amplification reactions were performed with AmpliTaq Gold DNA polymerase (Perkin Elmer, Foster City, Calif.) with a "hot start" to help ensure amplification specificity. Each 50 μl reaction mixture contained 2.5 units of DNA polymerase, 5 μl of a 10-fold diluted DNA sample (160-190 ng DNA), 12.5 pmol of each primer (7 pmol for exon 7), 0.05 mM dNTPs (Boehringer Mannheim, Indianapolis, Ind.) and 5 μl of 10×PCR buffer containing 15 mM $MgCl_2$ (Perkin Elmer). PCR cycling parameters involved a 12 min "hot start" at 94° C., followed by 35 cycles (40 cycles for exon 7) of 94° C. for 30 s, 55° C. (68° C. for the exon 7) for 30 s and 45 s at 72° C.—with a final 10 min extension at 72° C.

DNA sequencing was used to identify heterozygous bases. Sequencing was performed in the Mayo Clinic Molecular Biology Core Facility with an Applied Biosystems Model 377 DNA sequencers and BigDye™ (Perkin Elmer, Foster City, Calif.) dye primer sequencing chemistry. In all cases, both DNA strands were sequenced.

Primers used in sequencing were tagged at the 5'-ends with M13 sequence tags. Locations of primers were chosen to avoid repetitive sequence and to ensure amplification specificity. The sequences and locations of each primer within the gene are listed in Table 1. All forward primers contained the M13 forward sequence (underlined), and all reverse primers contained the M13 reverse sequence (underlined) to make it possible to use dye primer DNA sequencing chemistry. "F" represents forward; "R," reverse; "U," upstream; "D," downstream; "I," intron; and "FR," flanking region. The numbering scheme for primers located in exons and the 5'-FR is based on the cDNA sequence, with the "A" at the translation initiation codon designated as (+1). Positions 5' and 3' to that location were assigned negative or positive numbers, respectively. Intron based primers were numbered on the basis of nucleotide distance from splice junctions, with (+1) as the first nucleotide at the 5'-end, and (−1) as the first nucleotide at the 3'-end of the intron.

The PolyPhred 3.0 and Consed 8.0 programs were used to analyze the DNA sequence chromatograms for polymorphic sites. The University of Wisconsin GCG software package, Version 10, also was used to analyze nucleotide sequence.

TABLE 1

PCR primers used for SULT1E1 resequencing and site-directed mutagenesis

| Primer Name | Primer Location | Primer Specific | Sequence Gene Specific Primer-3' | SEQ ID NO: |
|---|---|---|---|---|
| Gene resequencing primers | | | | |
| UF(−289) | M13 5'-FR | | TGTAAAACGACGGCCAGTGC AGGATATTTCTACATCTCCA TGAATGAACATGACT | 8 |
| I1R(147) | Intron 1 | | CAGGAAACAGCTATGACCGC TTCACATCATTAATTTAACT AAAGTATCAAATCAAGACTT TGGTC | 9 |
| I1F(−170) | Intron 1 | | TGTAAAACGACGGCCAGTCT CTCTAGTTACCCAAACTATT TGATATGCAACTTTGC | 10 |
| I2R(145) | Intron 2 | | CAGGAAACAGCTATGACCGA GCTACCTTTTCTATGTCCAT ATCCAAACTACCG | 11 |
| I2F(−151) | Intron 2 | | TGTAAAACGACGGCCAGTAT AGAAAATATTTCCTGAGTCT GTGGCTATTCAGACACC | 12 |
| I3R(122) | Intron 3 | | CAGGAAACAGCTATGACCGC TGTCTTATGTAGAAGACCTG ATACTAATTGCCATTC | 13 |
| I3F(−196) | Intron 3 | | TGTAAAACGACGGCCAGTTA GGCATGCAATGCATAATAAT TACACCATGGGGAATG | 14 |
| I4R(185) | Intron 4 | | CAGGAAACAGCTATGACCTG GCAAAAGACAGAGTTGGAAT TAAAATATAGACTCTCTGAC | 15 |
| I4F(−183) | Intron 4 | | TGTAAAACGACGGCCAGTAA ACCACTGTCACCTCAGGTTA TGAAGATGTCTT | 16 |
| I5R(134) | Intron 5 | | CAGGAAACAGCTATGACCAT GCTTGCTCTTAAACCTCCAG GCCCCTTAGA | 17 |
| I5F(−171) | Intron 5 | | TGTAAAACGACGGCCAGTCA TGCTTTGCCTCTCTTGCTGG AGAGAACCT | 18 |
| I6R(167) | Intron 6 | | CAGGAAACAGCTATGACCGC TTCAAATCTATGCTAAAGTA TCTGTATTATTTTGGTCCTT TCC | 19 |
| I6(−160) | Intron 6 | | TGTAAAACGACGGCCAGTCA CAGCTTTTATAAAATTCCCC CAATTAGATTTCTCATTAGA AATC | 20 |
| I7R(132) | Intron 7 | | CAGGAAACAGCTATGACCTC AAATATGAAAGACTGCTGAA GAAAACTTAAGCTGGGTT | 21 |
| I7F(−170) | Intron 7 | | TGTAAAACGACGGCCAGTCA TCTTTGTAAGCCCCCAAAAG TATATCATTAAAGGTATAC | 22 |

TABLE 1-continued

PCR primers used for SULT1E1 resequencing and site-directed mutagenesis

| Primer Name | Primer Location | Primer Sequence Gene Specific Primer-3' | SEQ ID NO: |
|---|---|---|---|
| DR83 | 3'-FR | CAGGAAACAGCTATGACCAG TTAAACAAAAATTTAAAAAG AAAATGTCAACATAATCCA TGA | 23 |

Primers for site-directed mutagenesis

| | | | |
|---|---|---|---|
| F(−12) | Exon 1 | TGTAAAACGACGGCCAGTCA GTGTACCACAATGAATTCTG | 24 |
| R890 | Exon 7 | CAGGAAACAGCTATGACCCC TTCTTAGATCTCAGTTCGAA | 25 |
| F48 | Exon 2 | TGTAAAACGACGGCCAGTGA TTCTAATGTATAAAtATTTT GTCAAATATTG | 26 |
| R80 | Exon 2 | CAGGAAACAGCTATGACCCA ATATTTGACAAAATaTTTAT ACATTTAGAATC | 27 |
| F81 | Exon 2 | TGTAAAACGACGGCCAGTGG ATAATGTGGAAGtGTTCCAG GCAAGAC | 28 |
| R109 | Exon 2 | CAGGAAACAGCTATGACCGT CTTGCCTGGAACaCTTCCAC ATTATCC | 29 |
| F743 | Exon 7 | TGTAAAACGACGGCCAGTCC AGAAATTGTCGCaCTTCATG AGAAAGG | 30 |
| R772 | Exon 7 | CAGGAAACAGCTATGACCCC TTTCTCATGAAGtGCGACAA TTTCTGG | 31 |

Example 2

SULT1E1 Polmorphisms

The eight separate SULT1E1 PCR amplifications performed for each of the 120 individual human genomic DNA samples studied generated approximately 729,120 base pairs of sequence. The sequences were analyzed by use of the PolyPhred software.

All of the sequences analyzed were sequenced on both strands, making it possible to use data from the opposite strand to verify polymorphism calls. All sequences were compared to the SULT1E1 gene sequences of GenBank accession numbers U08098 and U20514-U20521.

Sequencing of the 5'- and 3'-untranslated sequences, exons, and introns of the SULT1E1 nucleic acid revealed 23 variations (Table 2); fifteen were found in introns, six were found in exons, and two were found in the 5'-flanking region. Polymorphisms in exons, untranslated regions (UTR), and flanking regions (FR) are numbered relative to the adenine in the SULT1E1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1). Asterisks indicate insertions or deletions. The average number of polymorphisms present both in the gene overall and within the ORF was 7.6 per kilobase sequenced.

The lowest allele frequency that was possible to detect was 0.8% because 60 DNA samples (120 alleles) were used. Those frequencies also are listed in Table 2. For African-Americans, thirteen of the eighteen polymorphisms had allele frequencies greater than 1% and, as a result, may be considered "common" in the African-American population sample. For Caucasian-Americans, eight of the thirteen polymorphisms had allele frequencies greater than 1% and may be considered "common" in the Caucasian-American population sample. Four of the polymorphisms observed in each of the African-American and Caucasian-American populations had allele frequencies greater than 10%. Six polymorphisms that were considered common in the African-American population (I1(−120), I3(−137), I4(139), E5(459), I5(55), and I7(−63)) were not detected in the Caucasian population, while one common polymorphism observed in the Caucasian population, I6(−39), was not detected in the African-American population.

TABLE 2

Human SULT1E1 polymorphisms and frequencies

| | | | Variant Sequence | | | |
|---|---|---|---|---|---|---|
| | | WT | | | Frequency | |
| Polymorphism Position | Location In Gene | Sequence Nucleotide | Nucleotide | Amino Acid Change | African-American | Caucasian-American |
| −232 | 5'-FR | G | A | | 0.008 | 0.0 |
| −190 | 5'-FR | C | G | | 0.008 | 0.0 |
| −64 | Exon 1 | G | A | | 0.2 | 0.067 |
| 69 | Intron 1 | A | G | | 0.225 | 0.492 |
| −73 | Intron 1 | G | C | | 0.3 | 0.383 |
| −20 | Intron 1 | A | T | | 0.092 | 0.0 |
| 64 | Exon 2 | G | T | Asp22Tyr | 0.008 | 0.0 |
| 95 | Exon 2 | C | T | Ala32Val | 0.0 | 0.008 |
| 22 | Intron 2 | T | C | | 0.008 | 0.008 |
| 237 | Exon 3 | T | C | | 0.0 | 0.008 |

TABLE 2-continued

Human SULT1E1 polymorphisms and frequencies

| Polymorphism Position | Location In Gene | WT Sequence Nucleotide | Variant Sequence Nucleotide | Amino Acid Change | Frequency African-American | Frequency Caucasian-American |
|---|---|---|---|---|---|---|
| −137 | Intron 3 | T | G | | 0.017 | 0.0 |
| −80 | Intron 3 | A | G | | 0.017 | 0.033 |
| 69 | Intron 4 | A | T | | 0.0 | 0.008 |
| 139 | Intron 4 | A | T | | 0.017 | 0.0 |
| −23 | Intron 4 | A | G | | 0.008 | 0.0 |
| 459 | Exon 5 | C | T | | 0.017 | 0.0 |
| 55 | Intron 5 | C | T | | 0.017 | 0.0 |
| −10 | Intron 5 | C | G | | 0.083 | 0.117 |
| 55 | Intron 6 | G | G Del | | 0.017 | 0.033 |
| −39 | Intron 6 | T | C | | 0.0 | 0.017 |
| 758 | Exon 7 | C | A | Pro253His | 0.0 | 0.008 |
| −121 | Intron 7 | C | T | | 0.333 | 0.108 |
| −63 | Intron 7 | T | G | | 0.017 | 0.0 |

Five SNPs were observed in the SULT1E1 coding region and one SNP (E1(−64)) in the UTR (Table 2 and FIG. 1). Two of the coding region SNPs were synonymous, i.e., they did not give rise to changes in amino acid sequence. The synonymous SNPs included E3(237) and E5(459). Three were non-synonymous, i.e., they gave rise to amino acid substitutions. These substitutions, at E2(64), E2(95), and E7(758), resulted in three different single variant SULT1E1 allozymes. One of the non-synonymous cSNPs, E2(64), was observed only in African-Americans. The other two, E2(95) and E7(758), were observed only in Caucasian-Americans. In addition to SNPs, one deletion event was observed in intron 6 of SULT1E1 (Table 2 and FIG. 1).

Example 3

Linkage Disequilibrium and Haplotype Analysis

Linkage disequilibrium analysis was performed after all of the DNA samples had been genotyped at each of the 23 polymorphic sites. Polymorphisms with p<0.05 were chosen for inclusion in this analysis, since there was inadequate statistical power for the analysis of less common polymorphisms. All possible pairwise combinations of these polymorphisms were tested for linkage disequilibrium using the EH program developed by Terwilliger and Ott (1994) *Handbook of Human Genetic Linkage*, The Johns Hopkins University Press, Baltimore, pp. 188-193. The output of this program was used to calculate d' values, a method for reporting linkage data that is independent of sample size (see Table 3).

The genotype data also were used for haplotype analysis. In this case, unambiguous haplotype assignment could be made for samples that contained no more than one heterozygous locus. Haplotypes for some of the remaining alleles were inferred from the genotype data as well as from EM probabilities (see Table 4; Long et al. (1995) *Am J Hum Genet*. 56:799-810; and Excoffier et al. (1995) *Mol Biol Evol* 12:921-927).

The twelve unambiguous haplotypes (those labeled *1) observed in the 120 resequenced DNA samples are listed. Nucleotides within each of the alleles that differed from the SULT1E1 consensus sequence (*1C) are shown in lowercase bold type. Initial designations of haplotypes were made on the basis of the encoded amino acid sequence, with the wild type sequence being designated *1. "Letter" designations were then added based on descending allele frequencies, starting with haplotypes present in both ethnic groups and then making assignments based on haplotypes observed in samples from African-American subjects. Although haplotypes could not be determined unequivocally, the Asp22Tyr variant is listed as *2, the Ala32Val variant as *3, and the Pro253His variant as *4.

TABLE 3

SULT1E1 linkage disequilibrium analysis

| Polymorphism Pair | | African-American d' Value | African-American p-Value | Caucasian-American d' Value | Caucasian-American p-Value |
|---|---|---|---|---|---|
| −232 | I3(−80) | 1 | 0.00694 | — | — |
| −232 | 459 | 1 | 0.006494 | — | — |
| −232 | I6(55) | 1 | 0.006494 | — | — |
| −232 | I7(−63) | 1 | 0.006494 | — | — |
| −64 | I1(−73) | −1 | 0.003557 | — | — |
| −64 | I7(−121) | 0.93 | 0 | 0.85 | 4e$^{-06}$ |
| I1(69) | I1(−73) | — | — | 0.65 | 1e$^{-06}$ |
| I1(69) | I5(−10) | 1 | 3e$^{-06}$ | 1 | 0.000506 |
| I1(−73) | I7(−121) | −1 | 3.6e$^{-05}$ | — | — |
| I3(−80) | I6(55) | 1 | 2.8e$^{-05}$ | 1 | 0 |
| I3(−80) | I6(−39) | — | — | 1 | 0.000544 |
| I4(−23) | I5(55) | 1 | 0.006494 | — | — |
| 459 | I7(−63) | 1 | 2.8e$^{-05}$ | — | — |
| I6(55) | I6(−39) | — | — | 1 | 0.000544 |

TABLE 4

SULT1E1 haplotype analysis

| Allele Designation | African-American | Caucasian-American | Exon 1 | | Intron 1 | | Exon 2 | Intron 4 | Intron 5 | | Exon 7 | Intron 7 |
|---|---|---|---|---|---|---|---|---|---|---|---|---|
| | | | −64 | 69 | −73 | −20 | 64 | 95 | 69 | 55 | −10 | 758 | −121 |
| *1A | 0.250 | 0.071 | G | A | c | A | G | C | A | C | C | C | C |
| *1B | 0.190 | 0.040 | a | A | G | A | G | C | A | C | C | C | t |
| *1C | 0.106 | 0.326 | G | A | G | A | G | C | A | C | C | C | C |
| *1D | 0.103 | 0.045 | G | A | G | A | G | C | A | C | C | C | t |
| *1E | 0.067 | 0.102 | G | g | G | A | G | C | A | C | g | C | C |
| *1F | 0.064 | — | G | A | G | t | G | C | A | C | C | C | C |
| *1G | 0.050 | 0.276 | G | g | c | A | G | C | A | C | C | C | C |
| *1H | 0.040 | — | G | g | G | A | G | C | A | C | C | C | t |
| *1I | 0.010 | — | a | A | G | A | G | C | A | C | C | C | C |
| *1J | 0.008 | — | G | A | G | A | G | C | A | t | C | C | C |
| *1K | — | 0.045 | G | g | G | A | G | C | A | C | C | C | C |
| *1L | — | 0.009 | G | A | G | A | G | C | t | C | C | C | C |
| *2 | 0.008 | — | G | A | G | A | t | C | A | C | C | C | C |
| *3 | — | 0.008 | G | A | G | A | G | t | A | C | C | C | C |
| *4 | — | 0.008 | G | A | G | A | G | C | A | C | C | a | C |

Example 4

SULT1E1 Expression

Four different SULT1E1 expression constructs were generated using the pCR3.1 expression vector (Invitrogen, Carlsbad, Calif.). Three constructs were designed to express the three variant SULT1E1 polypeptides, while one construct was designed to express the wild type SULT1E1. All variant SULT1E1 cDNA sequences used to make the expression constructs were created by site directed mutagenesis using the QuickChange™ Site-Directed Mutagenesis Kit (Stratagene, La Jolla, Calif.). Primers are shown in Table 1. Each SULT1E1 cDNA was amplified by PCR and subcloned into the EcoRI restriction site of the eukaryotic expression vector pCR3.1. After subcloning, all inserts were sequenced to assure that no spurious nucleotide point mutations had been introduced during the PCR amplifications.

COS-1 cells were transfected with 7 µg of each expression construct using the TransFast™ reagent (Promega, Madison, Wis.) as suggested by the manufacturer (i.e., using a 1:1 charge ratio). As a control, a transfection also was performed with 7 µg "empty" pCR3.1, i.e., vector lacking an insert, to make it possible to correct for endogenous COS-1 cell SULT activity. Seven µg of the control plasmid pSV-β-galactosidase (Promega, Madison, Wis.) was co-transfected with each SULT1E1 construct to make it possible to correct for transfection efficiency. Two independent transfections, each consisting of three separate plates, were performed with each expression construct.

After 48 hours in culture, the transfected cells were harvested and high speed supernatant (HSS) cytosol preparations were prepared as described by Wood et al., (1994) *Biochem. Biophys. Res. Commun.* 198:1119-1127. Aliquots of these cytosol preparations were stored at −80° C. prior to the assay.

Example 5

Enzyme Assays

The HSS preparations of recombinant SULT1E1 variant proteins described above were used for the activity studies without any further purification. The protein concentration of each recombinant protein preparation was determined by the dye-binding method of Bradford with bovine serum albumin (BSA) as a standard. β-galactosidase activity in each of the COS-1 HSS preparations was measured with the β-galactosidase Enzyme Assay System (Promega, Madison, Wis.). SULT1E1 enzyme activity was measured with an assay that involves sulfate conjugation of a sulfate acceptor substrate, 17-β estradiol (E2), in the presence of [$^{35}$S]-3'-phosphoadenosine-5'-phosphosulfate (PAPS), the sulfate donor for the reaction. See Campbell et al. (1987) *Biochem. Pharmacol,* 36:1435-1446; Foldes and Meek (*Biochim. Biophys. Acta,* 327:365-374, 1973) or Hernandez et al. (*Drug Metab. Disposit.,* 20:413-422, 1992).

Briefly, 0.4 µM $^{35}$S-PAPS were used as the sulfate donor with 0.05 µM E2 as the sulfate acceptor substrate in 8 mM dithiothreitol, 1.25 mM MgCl$_2$, and 10 mM potassium phosphate buffer at pH 6.5. Blanks were samples that did not contain E2. Cytosol from COS-1 cells that had been transfected with empty pCR3.1 was used to correct for endogenous SULT activity. Because SULTs display profound substrate inhibition, E2 concentrations that ranged from $10^{-3}$ M to $10^{-8}$ M were tested with each recombinant allozyme to ensure that the assays were performed at E2 concentrations that yielded maximal activity for that allozyme. Enzyme activity was expressed as nanomoles (nmole) of sulfate conjugated product formed per hour of incubation and adjusted to a percentage of the wild type SULT1E1 enzyme activity (FIG. 4).

Apparent $K_m$ values for each allozyme were determined with both cosubstrates. Initial experiments used 10-fold serial dilutions of E2 that ranged from $10^{-3}$ to $10^{-9}$ M. Apparent $K_m$ values were calculated by using the method of Wilkinson with a computer program written by Cleland (see, Wilkinson (1961) *Biochem J* 80:324-332; and Cleland (1963) *Nature* 198:463-365). Maximal activity for all allozymes was found at E2 concentrations near 100 nM. A second set of experiments was performed in the presence of 0.4 µM PAPS using eight concentrations of E2 that varied from 3.1 nM to 400 nM. For determination of apparent $K_m$ values for PAPS, seven concentrations of PAPS that ranged from 2.7 nM to 150 nM were assayed in the presence of 50 nM E2.

Figure 4:
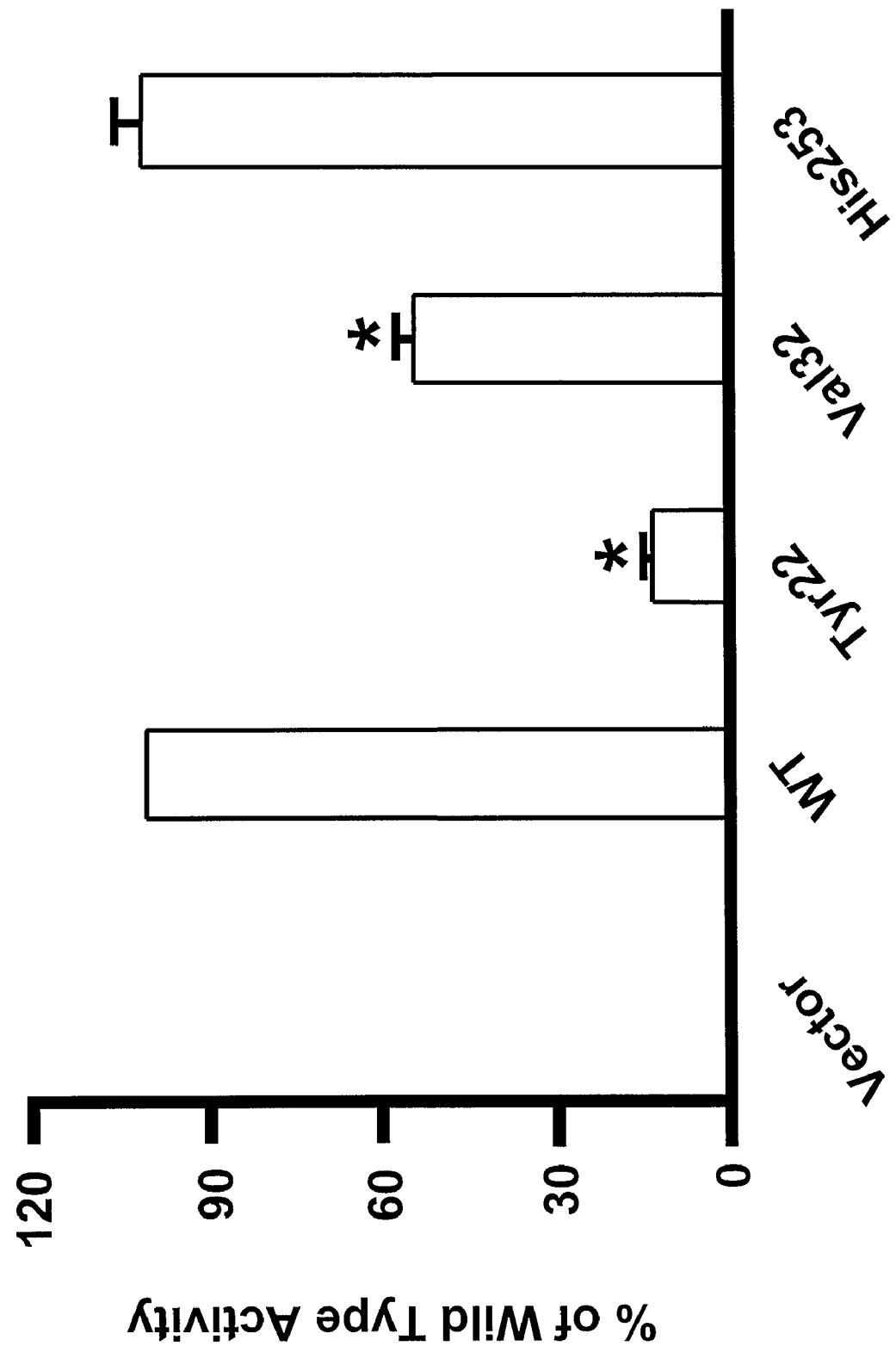
FIG. 4 is a graph plotting the activity levels of three SULT1E1 allozymes as a percent of the wild-type SULT1E1 enzyme activity.

Two of the three allozymes (Asp22Tyr and Ala32Val) exhibited significantly reduced levels of enzyme activity relative to the wild type SULT1E1 enzyme (FIG. 4). Although Ala32Val exhibited reduced activity (68.5% of wild-type), the apparent $K_m$ values of Ala32Val for estradiol and PAPS were comparable to those of the wild type SULT1E1 enzyme (Table 5). In contrast, although Asp22Tyr exhibited significantly reduced activity compared to the wild type enzyme (27% of wild-type), the apparent $K_m$ values of Asp22Tyr for estradiol and PAPS were 6 and 3.3 fold higher, respectively, than the wild type enzyme. The third allozyme (Pro253His) exhibited a level of activity that was similar to that of the wild type SULT1E1 enzyme (FIG. 4). The apparent $K_m$ values of Pro253His for estradiol and PAPS were approximately 2.5 and 2.8 fold higher, respectively, than the wild type SULT1E1 enzyme (Table 5).

Enzyme thermal stability was measured by diluting COS-1 cell supernatant preparations for each of the recombinant SULT1E1 allozymes and incubating them in a water bath for 15 minutes at temperatures ranging from 28° C. to 46° C. The samples were placed on ice immediately after incubation. Aliquots of the same supernatant preparations also were kept on ice as controls. Enzyme activity was measured in both heated and unheated samples, and blank values were determined for each temperature studied. $T_{50}$ values (i.e., values for temperatures resulting in 50% thermal inactivation, were calculated using the GraphPad Prism computer program (GraphPad Software, Inc., San Diego, Calif.). These studies revealed that the Asp22Tyr and Ala32Val allozymes had reduced $T_{50}$ values as compared to the wild-type enzyme, although the decrease for the Ala32Val allozyme was not statistically significant.

TABLE 5

Human SULT1E1 allozyme substrate kinetics and thermal stability

| SULT1E1 Allozyme | E2 as Varied Substrate | | | PAPS as Varied Substrate | | | Thermal Stability $T_{50}$ (° C.) |
|---|---|---|---|---|---|---|---|
| | Apparent $K_m$ (nM) | $V_{max}$ | $V_{max}/K_m \times (100)$ | Apparent $K_m$ (nM) | Vmax | $V_{max}/K_m \times (100)$ | |
| Wild type | $30.0 \pm 5.0^a$ | $26.8 \pm 4.4$ | 89.3 | $56.0 \pm 2.9^a$ | $27.2 \pm 0.7^a$ | 48.5 | $38.5 \pm 0.92$ |
| Asp22Tyr | $220 \pm 30.0^a$ | $4.7 \pm 0.3^b$ | 2.2 | $240 \pm 9.2^a$ | $1.9 \pm 0.1^a$ | 0.8 | $35.0 \pm 0.32^c$ |
| Ala32Val | $44.0 \pm 5.0^a$ | $22.8 \pm 6.6$ | 51.7 | $65.0 \pm 4.2^a$ | $5.7 \pm 0.1^a$ | 8.8 | $36.7 \pm 1.2$ |
| Pro253His | $97.0 \pm 7.0^a$ | $58.6 \pm 2.5^b$ | 60.4 | $180 \pm 7.5^a$ | $34.8 \pm 0.2^a$ | 19.3 | $38.4 \pm 0.46$ |

Values are expressed as mean ± SEM (n = 3).
$V_{max}$ is expressed as nmol/hr/β-galactosidase units.
[a] indicates that all values differed significantly from each other (P ≤ 0.04).
[b] indicates that values differed significantly from each other (P ≤ 0.01) except for the wild type and Ala32Val allozymes.
[c] indicates that the value differed significantly from the wild type and Pro253His allozymes (P ≤ 0.003).

Example 6

Western Blot Analysis

Quantitative Western blot analysis was performed using COS-1 cytosolic extracts containing recombinant SULT1E1 allozymes. The quantity of extracts loaded on 12.5% acrylamide gels was adjusted for each allozyme extract, so that each lane contained an equal quantity of β-galactosidase activity, i.e., gel loading was corrected for variation in transfection efficiency. The level of immunoreactive protein was measured using a rabbit polyclonal antibody directed against amino acids 1-13 of SULT1E1, with a cysteine residue added at the carboxy terminus. Properties of this antibody have been described elsewhere. See, Aksoy et al., (1994) *Biochem. Biophys. Res. Commun.* 200:1621-1629. Bound antibody was detected using the ECL system (Amersham Pharmacia, Piscataway, N.J.). An Ambis Radioanalytic Imaging System, Quant Probe Version 4.31 (Ambis, Inc., San Diego, Calif.) was used to quantitate immunoreactive protein in each lane, and the data were expressed as a percent of the intensity of the control wild type SULT1E1 protein band on that gel.

Figure 5:
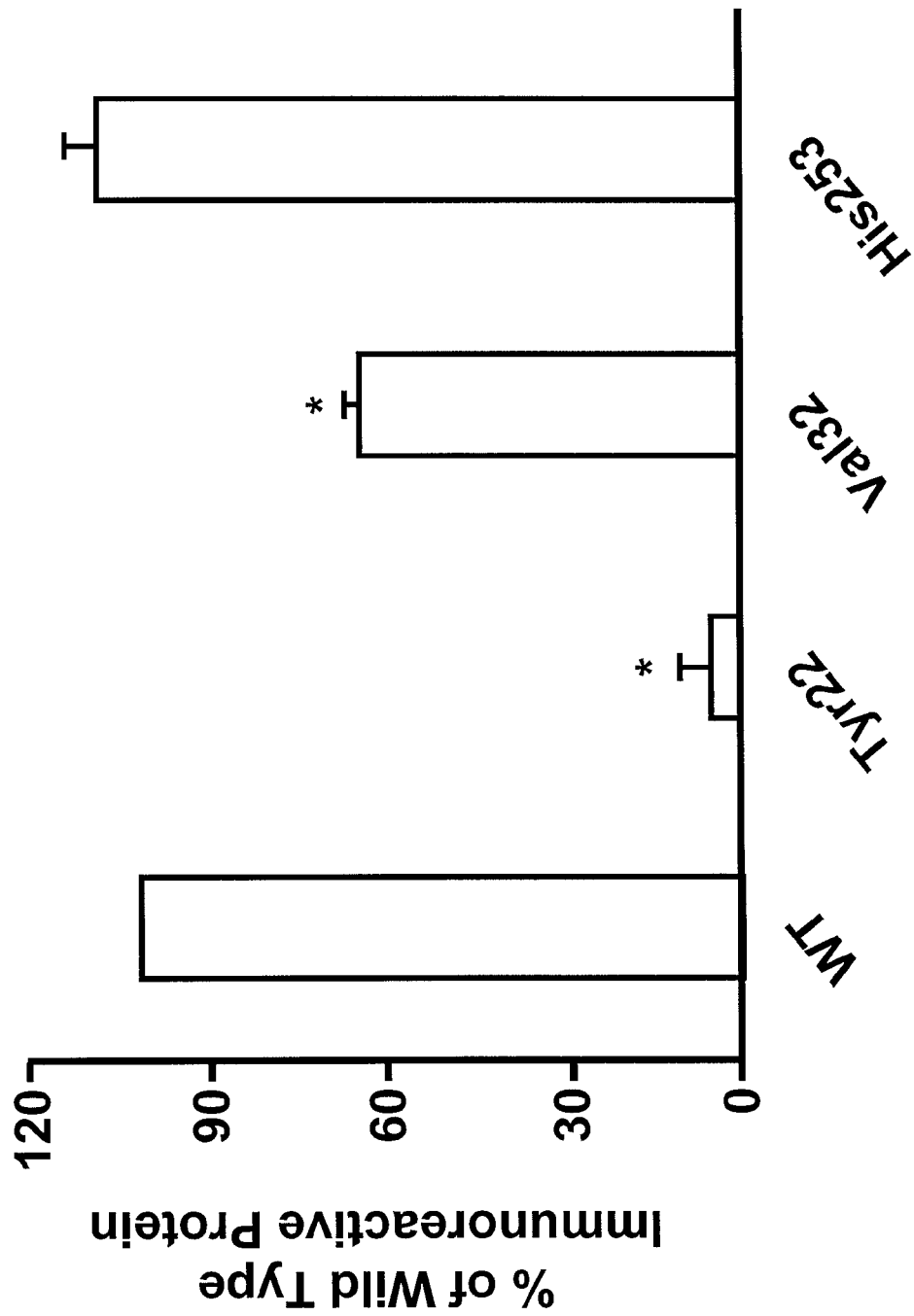
FIG. 5 is a graph plotting quantitative results of a western blot assay in which the amount of immunoreactive protein for each of three SULT1E1 allozymes was compared with the amount of immunoreactive protein for the wild-type SULT1E1 enzyme.

The average levels of immunoreactive SULT1E1 proteins, corrected for transfection efficiency, were correlated with the relative levels of enzyme activity for all three of the variant allozymes (FIGS. 4 and 5). Thus, the decreased activity of Asp22Tyr could be attributed both to alterations in the level of protein and to alterations in substrate kinetics (see Table 5 and FIG. 5). However, substrate kinetics for the Ala32Val allozyme were only slightly different from those of the wild-type enzyme. Thus, the decrease in enzyme activity for Ala32Val appeared to result primarily from a decreased level of immunoreactive protein. Although there were no differences in levels of either enzyme activity or immunoreactive protein for Pro253His, this allozyme did display significant increases in both $K_m$ and $V_{max}$ when compared with the wild-type enzyme—differences that may have "offset" each other in their effects on enzyme activity.

Example 7

SULT1E1 Polymorphisms and Crystal Structures

The x-ray crystal structure of mouse SULT1E1 has been solved in the presence of 3'-phosphoadenosine 5'-phosphate at a resolution of 2.5 Å (Kakuta et al. (1997) *Nature Struct. Biol.* 4:904-908). Recently, Pederson et al. (Pederson et al. (2002) *J. Biol. Chem.* 277:17928-17932) also solved the crystal structure of human SULT1E1 and reported that the substrate binding pocket of human SULT1E1 is very similar to that of the mouse enzyme. The Asp22Tyr polymorphism disclosed herein was located 14 residues downstream from the E2 substrate binding region, a conserved SULT "Region I" sequence motif (Weinshilboum and Otterness, "Sulfotransferase enzymes." In: Kaufmann (ed.), *Conjugation-Deconjugation Reactions in Drug Metabolism and Toxicity, chapter 2,* "Handbook of Experimental Pharmacology" series, volume 112, pp. 45-78. Berlin Heidelberg: Springer-Verlag, 1994; Varin et al. (1995) *Proc. Natl. Acad. Sci. USA* 89:1286-1290; and Weinshilboum et al. (1997) *FASEB J* 11:3-14). Since that polymorphism affected a residue located at the entrance to the substrate binding pocket, the change in amino acid might influence access of the substrate to the active site—a possible explanation for the observed increase in apparent $K_m$ value (Table 5). In contrast, the Ala32Val polymorphism resulted in both decreased enzyme activity and decreased immunoreactive protein (FIGS. 4 and 5), but it did not affect substrate kinetics (Table 5). On the basis of the x-ray crystal structure, that amino acid was located on the surface of the protein outside the putative substrate binding site. The third change in amino acid, Pro253His, was located 3 amino acids upstream of the "Region IV" conserved SULT sequence motif, the PAPS binding site (Weinshilboum and Otterness, supra; Varin et al., supra; and Weinshilboum et al., supra). This final polymorphism resulted in a 2 to 3 fold increase in $K_m$ and $V_{max}$ values for both E2 and PAPS (Table 5).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting of: (a) twenty to 100 contiguous nucleotides of SEQ ID NO: 6, wherein said sequence includes the nucleotide at position 201 of SEQ ID NO: 6, with the proviso that the nucleotide at position 201 is thymine; or (b) the complement of (a).

2. A vector comprising the nucleic acid molecule of claim 1.

3. An article of manufacture comprising a substrate, wherein said substrate comprises the isolated nucleic acid molecule of claim 1.

4. An isolated nucleic acid molecule consisting of: (a) twenty to 100 contiguous nucleotides of SEQ ID NO: 6, wherein said sequence includes the nucleotide at position 201 of SEQ ID NO: 6, with the proviso that the nucleotide at position 201 is thymine; or (b) the complement of (a), and, with respect to a) or b), a label.

5. The isolated nucleic acid molecule of claim 4, wherein said label is a fluorescent moiety.

6. The isolated nucleic acid molecule of claim 4, wherein said label is biotin.

7. A vector comprising the nucleic acid molecule of claim 4.

8. An article of manufacture comprising a substrate, wherein said substrate comprises the isolated nucleic acid molecule of claim 4.

* * * * *

UNITED STATES PATENT AND TRADEMARK OFFICE
CERTIFICATE OF CORRECTION

PATENT NO. : 7,803,921 B2  Page 1 of 1
APPLICATION NO. : 11/861075
DATED : September 28, 2010
INVENTOR(S) : Araba A. Adjei et al.

It is certified that error appears in the above-identified patent and that said Letters Patent is hereby corrected as shown below:

Column 51, line 52 (Claim 1), please delete "sequence" and insert --nucleic acid molecule-- therefor.

Column 51, line 62 (Claim 4), please delete "sequence" and insert --nucleic acid molecule-- therefor.

Signed and Sealed this

Seventh Day of December, 2010

David J. Kappos
*Director of the United States Patent and Trademark Office*